US010614289B2

(12) United States Patent
Senechal et al.

(10) Patent No.: US 10,614,289 B2
(45) Date of Patent: Apr. 7, 2020

(54) FACIAL TRACKING WITH CLASSIFIERS

(71) Applicant: Affectiva, Inc., Waltham, MA (US)

(72) Inventors: Thibaud Senechal, Cambridge, MA (US); Rana el Kaliouby, Milton, MA (US); Panu James Turcot, San Francisco, CA (US)

(73) Assignee: Affectiva, Inc., Boston, MA (US)

( * ) Notice: Subject to any disclaimer, the term of this patent is extended or adjusted under 35 U.S.C. 154(b) by 516 days.

(21) Appl. No.: 14/848,222

(22) Filed: Sep. 8, 2015

(65) Prior Publication Data
US 2016/0004904 A1  Jan. 7, 2016

Related U.S. Application Data

(63) Continuation-in-part of application No. 13/153,745, filed on Jun. 6, 2011, now abandoned, and a (Continued)

(51) Int. Cl.
*G06K 9/00* (2006.01)
*G06K 9/62* (2006.01)
(Continued)

(52) U.S. Cl.
CPC ..... *G06K 9/00228* (2013.01); *G06K 9/00268* (2013.01); *G06K 9/627* (2013.01);
(Continued)

(58) Field of Classification Search
CPC ............... G06K 9/00228; G06K 9/627; G06F 19/3418; G06F 19/3443; G06F 19/3481; G06F 9/00268
(Continued)

(56) References Cited

U.S. PATENT DOCUMENTS 3,034,500 A   5/1962  Backster, Jr.
3,548,806 A   12/1970 Fisher
(Continued)

FOREIGN PATENT DOCUMENTS

JP           08115367        7/1996
KR    10-2005-0021759 A     3/2005
(Continued)

OTHER PUBLICATIONS

El Maghraby, Amr, et al. "Detect and analyze face parts information using Viola-Jones and geometric approaches." Int. J. Comput. Appl 101.3 (2014): 23-28.*
(Continued)

*Primary Examiner* — Jonathan S Lee
(74) *Attorney, Agent, or Firm* — Adams Intellex, PLC

(57) ABSTRACT

Concepts for facial tracking with classifiers is disclosed. One or more faces are detected and tracked in a series of video frames that include at least one face. Video is captured and partitioned into the series of frames. A first video frame is analyzed using classifiers trained to detect the presence of at least one face in the frame. The classifiers are used to initialize locations for a first set of facial landmarks for the first face. The locations of the facial landmarks are refined using localized information around the landmarks, and a rough bounding box that contains the facial landmarks is estimated. The future locations for the facial landmarks detected in the first video frame are estimated for a future video frame. The detection of the facial landmarks and estimation of future locations of the landmarks are insensitive to rotation, orientation, scaling, or mirroring of the face.

26 Claims, 16 Drawing Sheets

Related U.S. Application Data continuation-in-part of application No. 14/460,915, filed on Aug. 15, 2014, which is a continuation-in-part of application No. 13/153,745, filed on Jun. 6, 2011, now abandoned.

(60) Provisional application No. 62/047,508, filed on Sep. 8, 2014, provisional application No. 62/082,579, filed on Nov. 20, 2014, provisional application No. 62/128,974, filed on Mar. 5, 2015, provisional application No. 61/352,166, filed on Jun. 7, 2010, provisional application No. 61/388,002, filed on Sep. 30, 2010, provisional application No. 61/414,451, filed on Nov. 17, 2010, provisional application No. 61/439,913, filed on Feb. 6, 2011, provisional application No. 61/447,089, filed on Feb. 27, 2011, provisional application No. 61/447,464, filed on Feb. 28, 2011, provisional application No. 61/467,209, filed on Mar. 24, 2011, provisional application No. 61/867,007, filed on Aug. 16, 2013, provisional application No. 61/924,252, filed on Jan. 7, 2014, provisional application No. 61/916,190, filed on Dec. 14, 2013, provisional application No. 61/927,481, filed on Jan. 15, 2014, provisional application No. 61/953,878, filed on Mar. 16, 2014, provisional application No. 61/972,314, filed on Mar. 30, 2014, provisional application No. 62/023,800, filed on Jul. 11, 2014.

(51) Int. Cl.
*G16H 50/70* (2018.01)
*G16H 20/30* (2018.01)
*G16H 50/50* (2018.01)
*G16H 50/20* (2018.01)

(52) U.S. Cl.
CPC .............. *G16H 20/30* (2018.01); *G16H 50/20* (2018.01); *G16H 50/50* (2018.01); *G16H 50/70* (2018.01)

(58) Field of Classification Search
USPC ........................................................ 382/103
See application file for complete search history.

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gera |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,091,334 A | 7/2000 | Galiana et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ballet et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,792,458 B1 | 9/2004 | Muret et al. |
| 6,847,376 B2 | 1/2005 | Engeldrum et al. |
| 7,003,135 B2 | 2/2006 | Hsieh et al. |
| 7,013,478 B1 | 3/2006 | Hendricks et al. |
| 7,050,607 B2 * | 5/2006 | Li ..................... G06K 9/00228 382/118 |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,747,801 B2 | 6/2010 | Han et al. |
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |

(56) References Cited

U.S. PATENT DOCUMENTS

| | | |
|---|---|---|
| 7,921,036 B1 | 4/2011 | Sharma |
| 8,010,458 B2 | 8/2011 | Galbreath et al. |
| 8,022,831 B1 | 9/2011 | Wood-Eyre |
| 8,219,438 B1 | 7/2012 | Moon et al. |
| 8,401,248 B1 | 3/2013 | Moon et al. |
| 8,442,638 B2 | 5/2013 | Libbus et al. |
| 8,522,779 B2 | 9/2013 | Lee et al. |
| 8,600,120 B2 | 12/2013 | Gonion et al. |
| 8,640,021 B2 | 1/2014 | Perez et al. |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0093784 A1 | 5/2003 | Dimitrova et al. |
| 2003/0182123 A1 | 9/2003 | Mitsuyoshi |
| 2003/0191682 A1 | 10/2003 | Shepard et al. |
| 2003/0191816 A1 | 10/2003 | Landress et al. |
| 2004/0181457 A1 | 9/2004 | Biebesheimer |
| 2005/0187437 A1 | 8/2005 | Matsugu |
| 2005/0210103 A1* | 9/2005 | Rui .................... G06K 9/00234 709/204 |
| 2005/0283055 A1 | 12/2005 | Shirai et al. |
| 2005/0289582 A1 | 12/2005 | Tavares et al. |
| 2006/0019224 A1 | 1/2006 | Behar et al. |
| 2006/0143647 A1 | 6/2006 | Bill |
| 2006/0170945 A1 | 8/2006 | Bill |
| 2006/0235753 A1 | 10/2006 | Kameyama |
| 2007/0076922 A1* | 4/2007 | Living ................ G06K 9/00295 382/118 |
| 2007/0167689 A1 | 7/2007 | Ramadas et al. |
| 2007/0173733 A1 | 7/2007 | Le et al. |
| 2007/0239787 A1 | 10/2007 | Cunningham et al. |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0184170 A1 | 7/2008 | Periyalwar |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1 | 11/2008 | Kurtz et al. |
| 2009/0002178 A1 | 1/2009 | Guday et al. |
| 2009/0006206 A1 | 1/2009 | Groe |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0150919 A1 | 6/2009 | Lee et al. |
| 2009/0164132 A1 | 6/2009 | Jung et al. |
| 2009/0193344 A1 | 7/2009 | Smyers |
| 2009/0210290 A1 | 8/2009 | Elliott et al. |
| 2009/0217315 A1 | 8/2009 | Malik et al. |
| 2009/0259518 A1 | 10/2009 | Harvey |
| 2009/0263022 A1* | 10/2009 | Petrescu ............ G06K 9/00234 382/195 |
| 2009/0270170 A1 | 10/2009 | Patton |
| 2009/0271417 A1 | 10/2009 | Toebes et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0266213 A1 | 10/2010 | Hill |
| 2010/0274847 A1 | 10/2010 | Anderson et al. |
| 2010/0324437 A1 | 12/2010 | Freeman |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |
| 2012/0324491 A1 | 12/2012 | Bathiche et al. |
| 2013/0023337 A1 | 1/2013 | Bowers et al. |
| 2013/0044958 A1* | 2/2013 | Brandt .................. G06T 5/005 382/201 |
| 2013/0116587 A1 | 5/2013 | Sornmo et al. |
| 2013/0121584 A1* | 5/2013 | Bourdev ............ G06K 9/00281 382/190 |
| 2013/0197409 A1 | 8/2013 | Baxter et al. |
| 2014/0172910 A1 | 6/2014 | Jung et al. |
| 2015/0154441 A1* | 6/2015 | Zhang ................ G06K 9/00221 382/118 |
| 2016/0104486 A1 | 4/2016 | Penilla et al. |
| 2016/0371537 A1* | 12/2016 | He ..................... G06K 9/00281 |
| 2017/0003784 A1 | 1/2017 | Garg et al. |
| 2017/0017831 A1* | 1/2017 | Rollend ............ G06K 9/00228 |

FOREIGN PATENT DOCUMENTS

| | | |
|---|---|---|
| KR | 10-2008-0016303 A | 2/2008 |
| KR | 1020100048688 A | 5/2010 |
| WO | WO 20111045422 A1 | 4/2011 |

OTHER PUBLICATIONS

Wang, Chao, and Xubo Song. "Tracking facial feature points with prediction-assisted view-based active shape model." Automatic Face & Gesture Recognition and Workshops (FG 2011), 2011 IEEE International Conference on. IEEE, 2011.*

Du, Shaoyi, et al. "Rotated haar-like features for face detection with in-plane rotation." VSMM. 2006.*

Ferry, Quentin, et al. "Diagnostically relevant facial gestalt information from ordinary photos." Elife 3 (2014).*

Cardinaux, Fabien, Conrad Sanderson, and Sébastien Marcel. "Comparison of MLP and GMM Classifiers for Face Verification on XM2VTS." International Conference on Audio-and Video-based Biometric Person Authentication. Springer, Berlin, Heidelberg, 2003. (Year: 2003).*

Arca, Stefano, Paola Campadelli, and Raffaella Lanzarotti. "A face recognition system based on automatically determined facial fiducial points." Pattern recognition 39.3 (2006): 432-443. (Year: 2006).*

Rana Ayman El Kaliouby, Mind-reading machines: automated inference of complex mental states, Jul. 2005, University of Cambridge, Cambridge, United Kingdom.

International Search Report dated Nov. 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

(56) References Cited

OTHER PUBLICATIONS

Verkruysse, Wim, Lars O. Svaasand, and J. Stuart Nelson. "Remote plethysmographic imaging using ambient light." Optics express 16.26 (2008): 21434-21445.
Albiol, Alberto, et al. "Face recognition using HOG-EBGM." Pattern Recognition Letters 29.10 (2008): 1537-1543.
Viola, P., & Jones, M. (2001). Rapid object detection using a boosted cascade of simple features. In Computer Vision and Pattern Recognition, 2001. CVPR 2001. Proceedings of the 2001 IEEE Computer Society Conference on (vol. 1, pp. I-I). IEEE.

* cited by examiner

FACIAL TRACKING WITH CLASSIFIERS

RELATED APPLICATIONS

This application claims the benefit of U.S. provisional patent applications "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015. This application is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. This application is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014; the application is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. The foregoing applications are each hereby incorporated by reference in their entirety.

FIELD OF ART

This application relates generally to facial detection and more particularly to facial tracking with classifiers.

BACKGROUND

The examination of the human face can provide dynamic, varied, and plentiful information. Facial data conveys the identity of the person under observation and can later be used to confirm that identity. Facial information further conveys a mood and a mental state or mental states of a person. The capture and analysis of facial information data of a person is undertaken for a wide variety of purposes and practical applications, including determination of a range of emotions and mental states, facial recognition, motion capture, eye tracking, lie detection, computer animation, and other applications. The analysis of facial information data can also be used for the tracking of facial motions, gestures, gaze directions, head poses, expressions, and so on. The applications for the analysis of facial information are both varied and wide ranging, and include product and service market analysis, biometric and other identification, law enforcement applications, social networking connectivity, and healthcare processes, among many others. The analysis is often based on viewing a face, facial expressions, facial features, movements of facial muscles, etc. The results of the analysis can be used to determine emotional and mental states, identity, veracity, and so on, of the person or persons being analyzed. Facial analysis is often used for tracking purposes. The tracking component is often employed to locate a person or persons, and can be used to predict future movement and location of the person or persons. Such geographical tracking has many practical applications including sporting event coverage, law enforcement applications, disease propagation detection, computer gaming events, social networking connectivity, and so on.

Humans are particularly good at processing facial information data for a variety of purposes. Perhaps foremost among the varied purposes is social interaction. The social interaction can be among strangers, friends, family members, and so on. The facial processing is critical to personal safety and even survival in some cases, and is used for such basic human activities as social interactions including cooperation, locating a mate, etc. The facial processing is used to rapidly identify whether a stranger appears friendly and approachable or appears dangerous and should be avoided. Similarly, the processing can be used to quickly determine a friend's mood, the mental state of a family member, and so on. The processing of facial information data is used to draw attention to important objects or events in one's environment, such as potential sources of physical danger requiring an immediate and appropriate response.

Analysis of facial information data becomes difficult for people and for processors when the desired facial information data is captured along with other undesirable data. Imagine for example, that one friend is looking for another friend in a crowd at a sporting event, music concert, political convention, or other large group activity. The flood of spurious data that is captured simultaneously with the facial information data of the sought-after friend confounds the facial information data. This saturation of the facial information data complicates the search for the friend in the crowd. The spurious data must be separated from the facial information data in order to obtain the desired outcome, which in this case is the detection of one's friend in the crowd. The detection of one's friend is further complicated if the friend is moving along with the rest of the crowd. In this scenario, the friend may not be visible at all times, as he or she is moving in and out of sight among the crowd.

SUMMARY

Videos are collected from a plurality of people. The videos are partitioned into video frames, and video frames are analyzed to detect locations of facial points or facial landmarks. The locations of the facial points in a first video frame can be used to estimate the locations of facial points in future video frames. An output from a facial detector can be simulated based on the estimations of the locations of the facial points in the future video frames.

A computer-implemented method for facial tracking is disclosed comprising: obtaining a video that includes a face; performing face detection to initialize locations for facial points within a first frame from the video; refining the locations for the facial points based on localized information around the facial points; estimating future locations for the facial points for a future frame from the first; and simulating an output for a facial detector based on the estimating of the future locations for the facial points. The simulating can include generating a bounding box for the face.

In embodiments, a computer program product embodied in a non-transitory computer readable medium for facial detection comprises: code for obtaining a video that includes a face; code for performing face detection to initialize locations for facial points within a first frame from the video; code for refining the locations for the facial points based on localized information around the facial points; code for estimating future locations for the facial points for a future frame from the first; and code for simulating an output for a facial detector based on the estimating of the future locations for the facial points.

In some embodiments, a computer system for facial detection comprises: a memory which stores instructions; one or more processors attached to the memory wherein the one or more processors, when executing the instructions which are stored, are configured to: obtain a video that includes a face; perform face detection to initialize locations for facial points within a first frame from the video; refine the locations for the facial points based on localized information around the facial points; estimate future locations for the facial points for a future frame from the first; and simulate an output for a facial detector based on the estimating of the future locations for the facial points.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
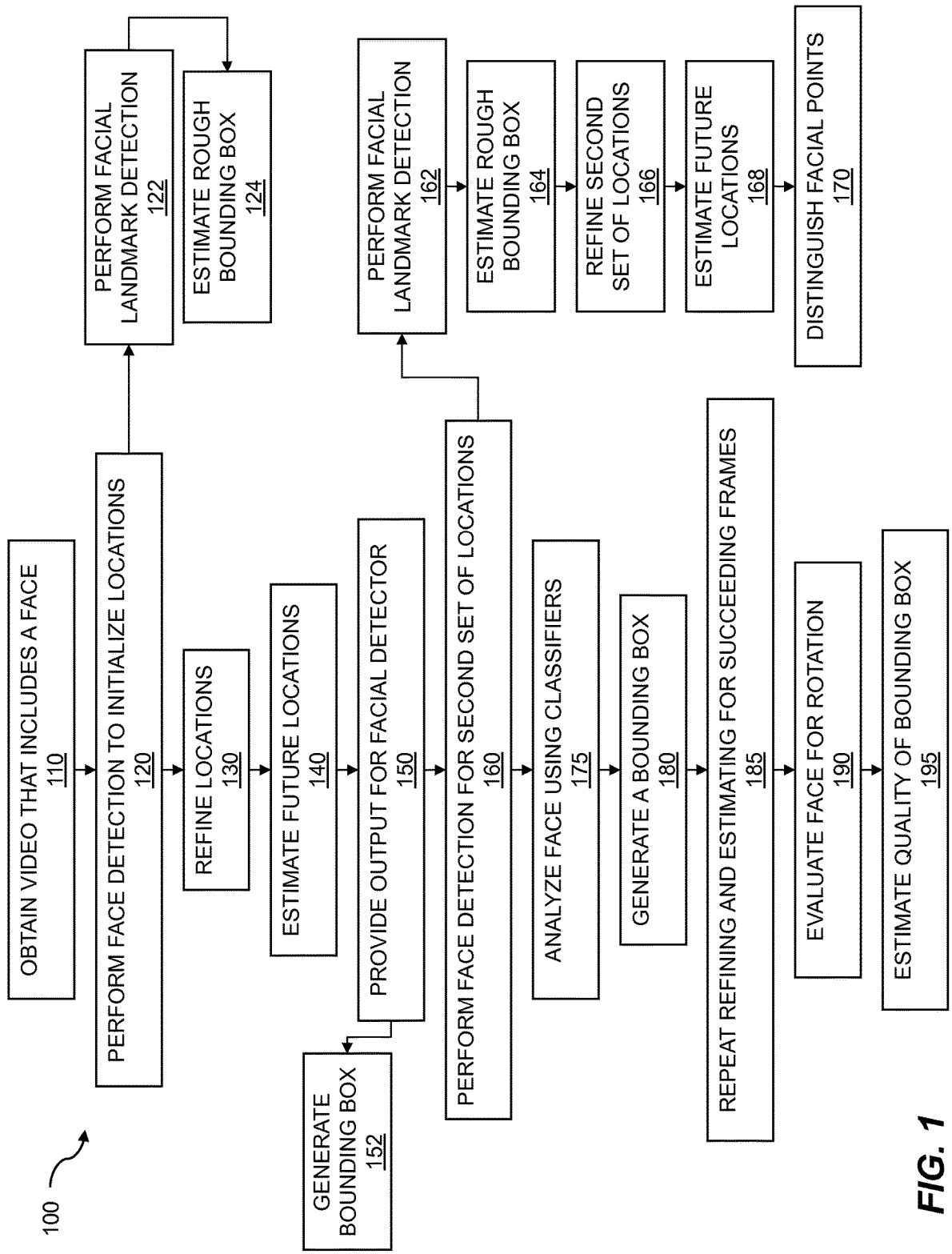
FIG. 1 is a flow diagram for facial tracking using classifiers.

Processing images is a key skill performed by humans in all areas of life. A person must process images such as black and white and color images; videos including slideshows, video clips, and full-length movies; and other electronic images almost constantly in today's modern, highly interactive and media-intensive society. However, the human ability to process visual stimuli stretches back far before the advent of multimedia images. The ability to distinguish between a non-essential and a pertinent image requires the human brain to make a series of evaluations. For example, a movement or flash, briefly viewed in peripheral vision, can trigger instant attention, interest, concern, and so on. Processing systems in the brain unconsciously coordinate a unified and rapid response that allows a person to identify the pertinent visual data and determine whether the stimulus presents physical danger. The ability to quickly locate the source of a movement or another event, to identify it, and to plan a reaction to is a crucial part of interacting with and functioning in the world.

Facial detection by a computing device is a technique by which a computer mirrors many of the unconscious processes of the human brain to process, evaluate, and categorize a myriad of images and videos. Facial detection can be used for purposes including finding a face in a scene, identifying a face, tracking a face, and so on. Facial detection finds wide-ranging applications in fields including healthcare, law enforcement, social media, gaming, and so on. Detected facial data also can be used to determine the mental and emotional states of the people whose faces have been detected, for example. The determined mental and emotional states can be used for identification and classification purposes, among others.

However, the processing of facial data can be a complex and resource-intensive computational problem. Consider, for example, an image, still or video, of a loved one. The human brain can quickly identify the important face in profile, in a portrait shot, in a crowd, rotated, or even in a decades-old image. Even though human facial detection is by no means foolproof—for example, siblings or even parents and children can be hard to distinguish in photographs taken at the same age—the speed and accuracy of the identification is often remarkable. As a result, automatic facial detection techniques must anticipate and perform many simultaneous tasks, making automated detection complex and not always successful when evaluating similar images.

Certain techniques, however, render automatic facial processing more effective and less computationally intensive. For example, facial tracking can be used to aid in the identification and processing of human faces in videos. In this technique, a given video can be partitioned into frames and all of the frames or a subset of the frames from the video can be analyzed. The analysis can include detecting a face within a first frame. When a face is detected, locations of facial points or landmarks can be initialized. The facial points can include facial features including locations of eyes, ears, a nose, a mouth, a chin, facial hair, and so on. The facial points can also include distinguishing marks and features on a face including a mole, a birthmark, a scar, etc. Based on the locations of the facial points within one video frame, the locations of the same facial features in a later frame from the video can be estimated. The later frame can be the next frame from the video or another frame from a different moment in the video. A facial detector can be simulated based on the estimated locations of the future facial points. The simulating of the facial detector can generate an output, where the output can include a bounding box for the face. The locations of the facial points in subsequent frames and of the bounding box can be adapted based on the actual location of the face in the later frames from the video. The adapted locations of the facial points and the bounding box can be used for other future frames from the video.

FIG. 1 is a flow diagram for facial tracking using classifiers. The flow 100 describes a computer-implemented method for facial detection. The facial detection can include pose estimation. The facial detection can be used for a variety of purposes including healthcare, gaming, facial recognition, biometrics, computer vision, law enforcement, and so on. The flow 100 includes obtaining a video that includes a face 110. The video can include more than one face, one or more objects, and so on. The video can be obtained using a camera where the camera can include a video camera, still camera, thermal imager, CCD device, phone camera, three-dimensional camera, depth camera, light field camera, multiple webcams used to show different views of a person, or any other type of image capture apparatus that can allow captured data to be used in an electronic system. The flow 100 includes performing face detection to initialize locations 120 for a first set of facial landmarks within a first frame from the video. The face detection can be based on other facial points, identifying characteristics, etc. The landmarks can include corners of the mouth, corners of eyes, eyebrow corners, tip of nose, nostrils, chin, tips of ears, distinguishing marks and features, and so on. Facial detection can be accomplished using a variety of techniques including edge detection, color image processing, landmark identification, and so on. The detection to initialize locations for a first set of facial landmarks can include performing facial landmark detection 122 within the first frame from the video. Similarly, detection to initialize locations for another set or sets of facial landmarks can be performed on any frame from the video. The detection to initialize locations for a first set of facial landmarks can also include estimating a rough bounding box 124 for the face based on the facial landmark detection. As before, estimating a rough bounding box for the face or other faces can be based on detection of any facial landmark, facial point, facial characteristic, distinguishing marks, etc. The bounding box can be a minimum bounding or encompassing box within which all of the facial landmarks can be included. The estimating of the rough bounding box can be based on box area, box volume, and so on.

The flow 100 includes refining the locations 130 for the first set of facial landmarks based on localized information around the first set of facial landmarks. The refining the locations of facial landmarks can include centering location points on the facial landmarks, where the facial landmarks can include corners of a mouth, corners of eyes, eyebrow corners, tip of nose, nostrils, chin, tips of ears, and so on. The refining of the locations for the facial points can include centering location points on facial attributes including eyes, ears, a nose, a mouth, a chin, etc. The refining can also include detection of the face within a background, for example. The refining can include identification of one face from among a plurality of faces in the frame from the video. The flow 100 includes estimating future locations 140 for landmarks within the first set of facial landmarks for a future frame from the first frame. The estimating future locations can include using the locations of facial points, facial landmarks, facial characteristics, distinguishing marks, etc. in a first frame to estimate the locations of facial points, facial landmarks, facial characteristics, distinguishing marks, etc. in a second frame, for example. The second frame can be a future (subsequent) frame or a past (previous) frame. The future frame can be a next frame in a chronological series of frames from the first frame in the video. The flow 100 includes providing an output for a facial detector 150 based on the estimating of the future locations for the landmarks. The providing an output for a facial detector can include estimating the future locations for the facial landmarks, facial points, facial characteristics, distinguishing marks, etc. The providing an output including the future locations for the facial landmarks, facial points, and so on, can be used to predict the presence and location of a face in a future frame, for example. The future frame can be the next frame in a series of frames, a later frame, and so on. The providing of the output of the facial detector can include generating a bounding box 152 for the face. A first bounding box can be generated for a face that is detected in a first frame. The first bounding box can be a square, a rectangle, and/or any other appropriate geometric shape. The first bounding box can be substantially the same as the bounding box generated by a face detector. The first bounding box can be a minimum-dimension bounding box, where the dimension can include area, volume, hyper-volume, and so on. The first bounding box can be generated based on analysis, estimation, simulation, prediction, and so on.

The flow 100 includes performing face detection to initialize a second set of locations 160 for a second set of facial landmarks for a second face within the video. The face detection of the second face can be based on other facial points, as described above. Facial detection of the second face can be accomplished using a variety of techniques including edge detection, color image processing, landmark identification, and so on. The performing face detection on the second face can include performing facial landmark detection 162 within the first frame from the video for the second face. As was the case for the detection of the first set of facial landmarks for the first face within the video, the facial landmarks for the second face can include corners of the mouth, corners of eyes, eyebrow corners, tip of nose, nostrils, chin, tips of ears, distinguishing marks and features, and so on. Other facial landmarks can also be used. The performing face detection on the second face includes estimating a second rough bounding box 164 for the second face based on the facial landmark detection. The second bounding box can be a square, a rectangle, and/or any other appropriate geometric shape. The second bounding box can be a different geometric shape from that of the first bounding box. The second bounding box can be substantially the same as the bounding box generated by a face detector. The second bounding box can be a minimum-dimension bounding box, where the dimension can include area, volume, hyper-volume, and so on. The second bounding box can be generated based on analysis, estimation, simulation, prediction, and other appropriate techniques. The performing face detection on the second face includes refining the second set of locations 166 for the second set of facial landmarks based on localized information around the second set of facial landmarks. The technique for refining of the locations of the second set of facial landmarks can be the same as or different from the refining of the locations of the first set of facial landmarks. The refining of the locations for the second set of facial landmarks can include centering location points on facial attributes such as facial points including eyes, ears, a nose, a mouth, a chin, etc., as well as refining the locations of facial landmarks that can include corners of a mouth, corners of eyes, eyebrow corners, tip of nose, nostrils, chin, tips of ears, and so on. The refining can also include detection of the second face within a background, for example. The performing face detection on the second face includes estimating future locations 168 for the second set of locations for the second set of facial landmarks for the future frame from the first frame. The estimating future locations for the second set of facial landmarks can include using the locations of facial points, facial landmarks, facial characteristics, distinguishing marks, etc. in a first frame to estimate the locations of facial points, facial landmarks, facial characteristics, distinguishing marks, etc. in a second frame, for example. The second frame can be a future (subsequent) frame or a past (previous) frame. The future frame can be a next frame in a chronological series of frames from the first frame in the video. The performing face detection on the second face includes distinguishing facial points 170 from the first face from other facial points. The distinguishing facial points can include distinguishing facial points from the second face, distinguishing facial points from a third face, and so on. The distinguishing facial points can include distinguishing the second set of facial points, second set of facial landmarks, second set of facial characteristics, second set of distinguishing marks, etc. from the first set of facial points, first set of facial landmarks, first set of facial characteristics, first set of distinguishing marks, and so on.

The flow 100 includes analyzing the face using a plurality of classifiers 175. The face that is analyzed can be the first face, the second face, the third face, and so on. The face can be analyzed to determine facial landmarks, facial features, facial points, and so on. The classifiers can be used to determine facial landmarks including corners of a mouth, corners of eyes, eyebrow corners, tip of nose, nostrils, chin, tips of ears, and so on. The plurality of classifiers can provide for analysis of gender, ethnicity, or age corresponding to the face. Classifiers can be used to provide for analysis of other demographic data and information.

The flow 100 further includes generating a bounding box 180 for the face within the first frame. The bounding box that is generated can be a square, a rectangle, and/or any other appropriate polygon for surrounding a shape with a frame. For example, the bounding box can be generated for a shape that is a face within a frame. The flow 100 includes repeating the refining and the estimating for succeeding frames 185 from the video. The repeating can be accomplished for one succeeding frame, a sequence of succeeding frames, a random selection of succeeding frames, and so on. The repeating can include one or more of the refining and the estimating. The flow 100 includes evaluating the face to determine rotation 190 about a z-axis of the face. The evaluating the face can be used to determine that a face has rotated from a first frame to a second frame, where the second frame can be a past frame, the previous frame, the next frame, a succeeding frame, and so on. The evaluating the face to determine rotation about the z-axis or another axis can determine a view of the face. For example, the view of the face can be a one quarter view, a half (profile) view, a three quarter view, a full view, and so on. The flow 100 includes estimating a quality of the rough bounding box 195 for the future frame. The estimating of the quality of the rough bounding box for future frames can be based on accuracy, percent error, and/or deviation, along with other factors, for the bounding box for a future frame. The estimating of the quality of the bounding box for future frames can be based on a threshold. Various steps in the flow 100 may be changed in order, repeated, omitted, or the like without departing from the disclosed concepts. Various embodiments of the flow 100 may be included in a computer program product embodied in a non-transitory computer readable medium that includes code executable by one or more processors. Various embodiments of the flow 100 may be included in a purpose-built customized processor, computer, and integrated circuit chip.

Figure 2:
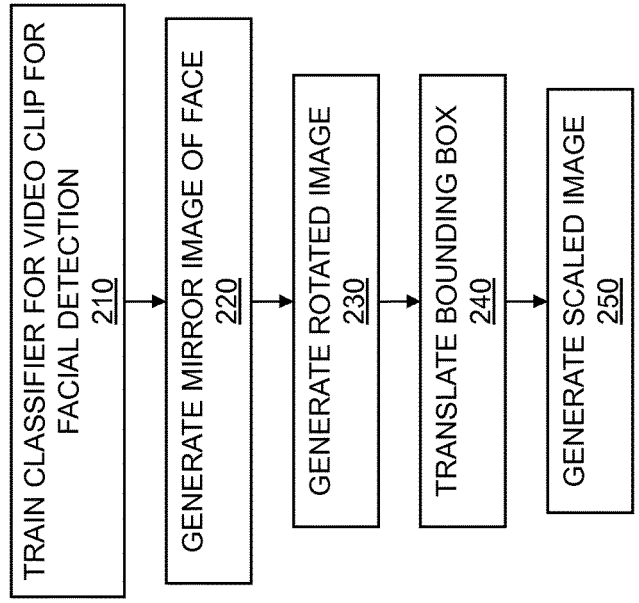
FIG. 2 is a flow diagram for classifier training.

FIG. 2 is a flow diagram for classifier training 200. Classifiers can be used for detection of facial landmarks, facial points, facial characteristics, and distinguishing marks; for analysis of gender, ethnicity, or age corresponding to the face; and so on. The facial landmarks that can be detected can include corners of a mouth, corners of eyes, eyebrow corners, tip of nose, nostrils, chin, tips of ears, and so on. Classifiers can be used to provide for analysis of other demographic data and information, for example. The flow 200 includes training a classifier for a video clip for facial detection 210. The video clip can be a portion of a video, a combination of frames, a slide from a slide show, and so on. The classifier can include a face, a facial expression, and so on. The training of a classifier can include machine learning to improve the accuracy of the classifier. The training of the classifier can be based on a linear support vector machine (SVM), a non-linear SVM, and so on. The training of the classifier can be based on using a "known good" data set, a test set, a set of training samples, or another data set. The training can include using a radial basis function (RBF) kernel or another technique. Computing a feature mapping with a lower dimension can approximate the RBF kernel. A linear SVM can learn in the feature space with the lower dimension. The feature mapping can be based on selecting a subset of training samples, where the training samples that are used for the training can be selected randomly. The selecting a subset of training samples can be based on using some randomness and some contextual information.

The contextual information can include video origin information from which a sample is extracted, a subject identification (ID), different expression information, and so on. The flow 200 includes generating a mirror image of the face 220. The generating of the mirror image of the face can be accomplished by rotating the image of the face 180 degrees at the centerline of the face, or by using another mirroring technique, for example. The flow 200 includes generating a rotated image 230 of the face. The rotated image of the face can be rotated by a constant amount, by a series of predetermined amounts, by a random amount, and so on. For example, the face can be rotated by 45 degrees; by a series of rotations including 5 degrees, 10 degrees, and 15 degrees; and so on. The face can be rotated by any appropriate amount for training purposes for training the one or more classifiers. The flow 200 includes translating the rough bounding box 240 to a different location. The translating the rough bounding box can be based on a random translation, a fixed translation, a pattern of translations, a predetermined translation, and so on. For example, a pattern of translations of the bounding box could include translating along the x-axis and y-axis (east, west, north, south), and diagonally (northwest, northeast, southeast, southwest) for up to eight other translations. The translation can be by a distance equal to a dimension of the bounding box, or by any other amount. The flow 200 includes generating a scaled image 250 of the face. The generating of the scaled image of the face can include enlarging the face (zooming in), shrinking the face (zooming out), and so on.

Figure 3:
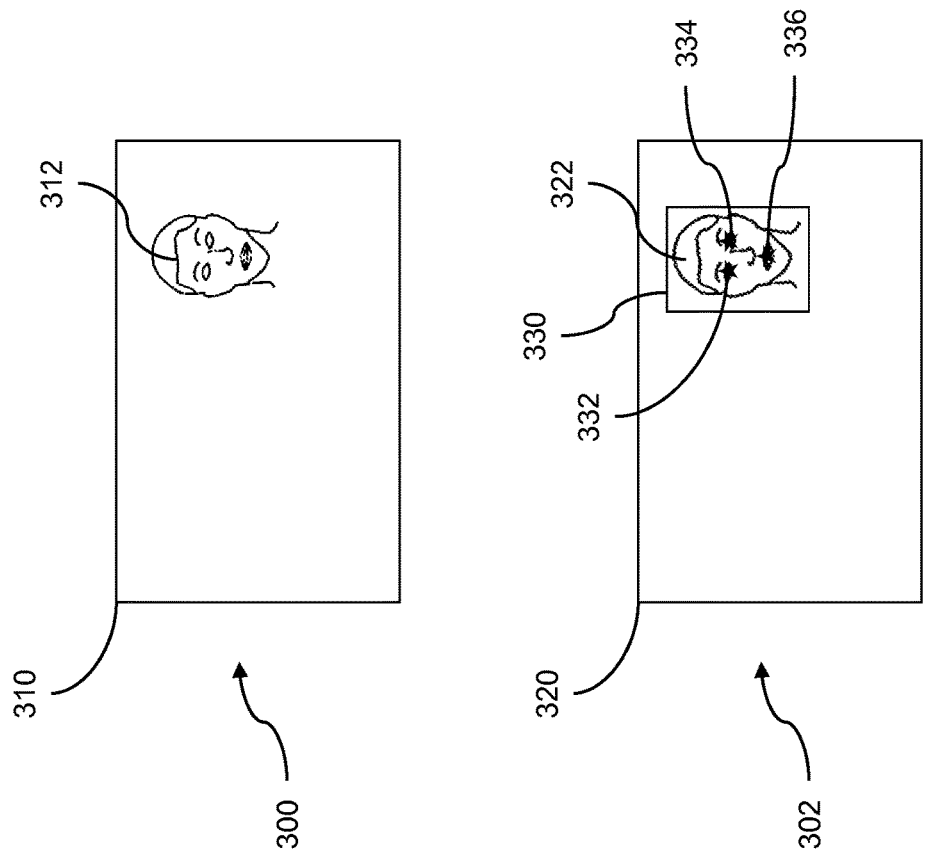
FIG. 3 shows example landmarks and bounding box generation.

FIG. 3 shows example landmarks and bounding box generation. A video containing a face of a person can be partitioned into one or more video frames. Video frames before landmark and bounding box generation 300 and after landmark and bounding box generation 302 are shown. The frame before generation 300 includes a frame boundary 310 and a face 312. The frame 300 is analyzed to generate facial landmarks and a bounding box. The frame after generation 302 includes a frame boundary 320 and a face 322 in addition to a bounding box 330 and locations of facial points 332, 334, and 336. While three facial points are shown, any number of facial points appropriate to a face tracking technique can be included. For example, the facial points 332 and 334 correspond to eyes on the face 322, and the facial point 336 corresponds to a mouth on the face 322. In other embodiments, the one or more facial points detected for the face 322 can include an eyebrow, a chin, an ear, distinguishing facial marks, and so on.

Figure 4:
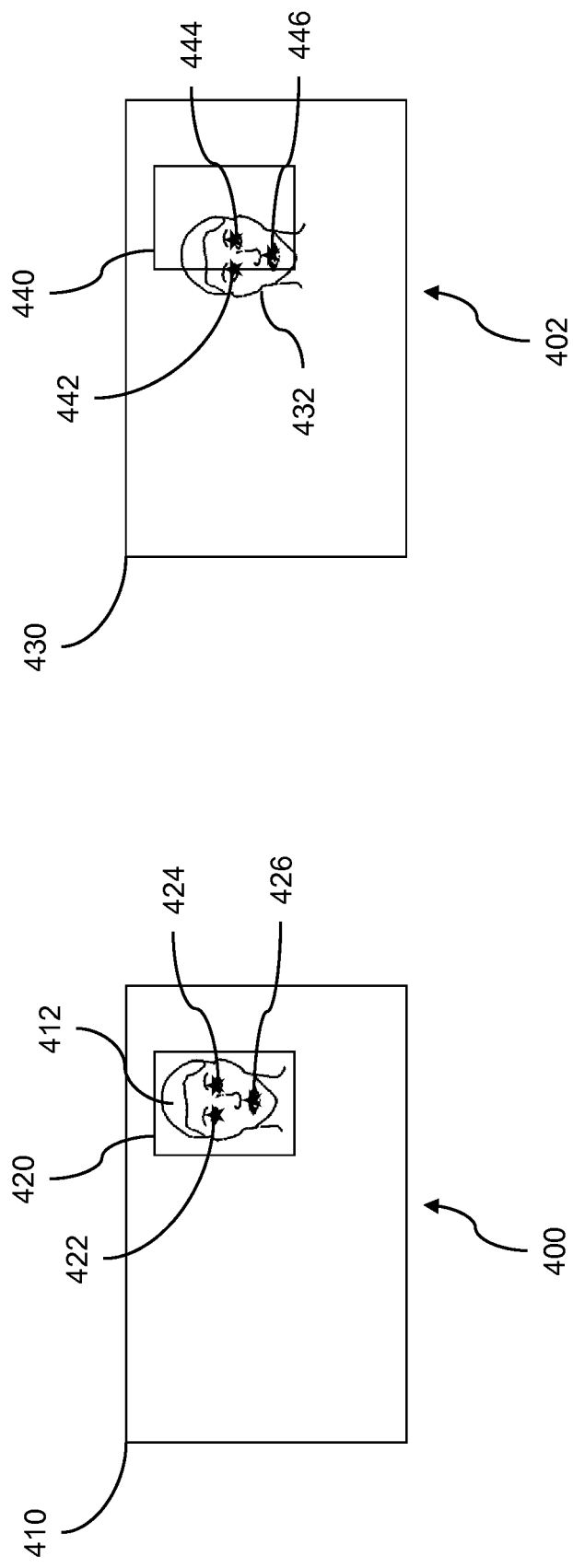
FIG. 4 illustrates the use of a bounding box and landmarks for a next frame.

FIG. 4 illustrates the use of a bounding box and landmarks for a next frame. As described above, a video containing a face of a person can be partitioned into a plurality of frames for analysis. A first video frame 400 shows a frame boundary 410, a face 412, a bounding box 420 and the facial points 422, 424, and 426 which can be generated for the frame 400. The bounding box and the facial points can be detected in the first video frame using any of a variety of detection techniques. While three facial points 422, 424, and 426 are shown, any number of facial points appropriate to facial tacking can be included. The bounding box 420 and the facial points 422, 424, and 426 can be used to estimate future locations of the facial points within a second frame based on the detection of the first frame. A second frame 402 is also shown. The second video frame 402 shows a frame boundary 430, a face 432, a bounding box 440 and the facial points 442, 444, and 446. While three facial points 442, 444, and 446 are shown, any number of facial points appropriate to facial tracking can be included. The location of the bounding box 440 can be estimated and can be based on the location of the generated bounding box 420 from the prior frame 400. The three facial points 442, 444, and 446 are detected based on the location of the face 432 in the second frame. The three facial points 442, 444, and 446 might or might not lie within the bounding box 440. Based on the accuracy of the estimating of the bounding box 440, a new estimation can be determined for a third, future frame from the video, and so on.

Figure 5:
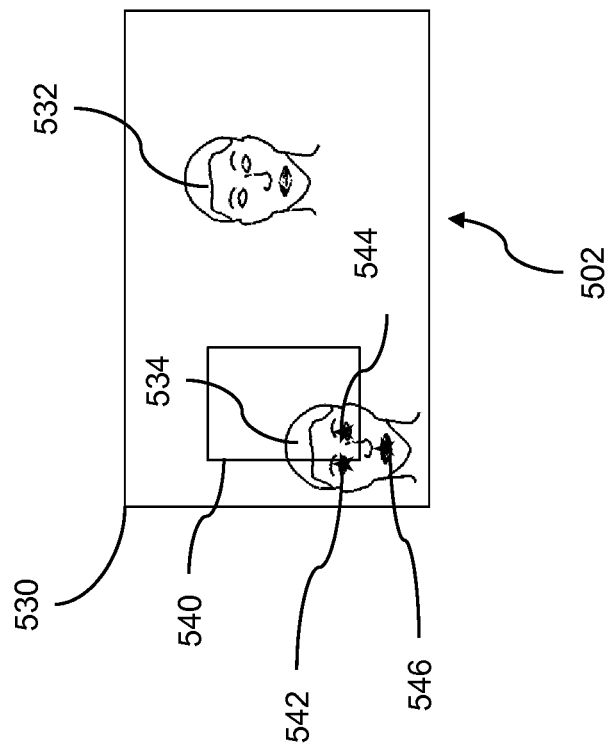
FIG. 5 shows an example performance of face detection for a second face.
Figure 5:
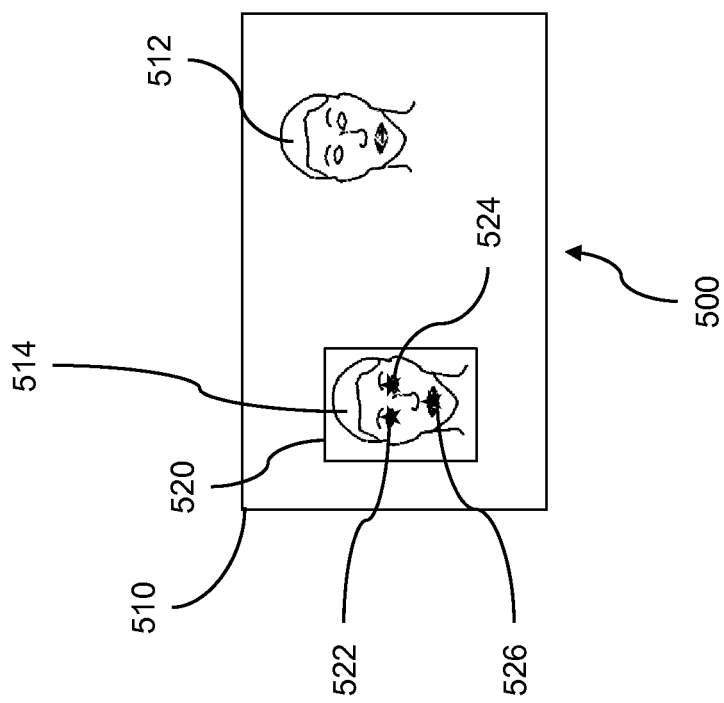

FIG. 5 shows an example performance of face detection for a second face as well as facial tracking One or more videos can be captured, where the videos contain one or more faces. The video or videos that contain the one or more faces can be partitioned into a plurality of frames, and the frames can be analyzed for the detection of the one or more faces. The analysis of the one or more video frames can be based on one or more classifiers. A classifier can be an algorithm, heuristic, function, or piece of code that can be used to identify into which of a set of categories a new or particular observation, sample, datum, etc. should be placed. The decision to place an observation into a category can be based on training the algorithm or piece of code, for example, by analyzing a known set of data, known as a training set. The training set can include data for which category memberships of the data can be known. The training set can be used as part of a supervised training technique. If a training set is not available, then a clustering technique can be used to group observations into categories. This latter approach or unsupervised learning can be based on a measure (i.e. distance) of one or more inherent similarities among the data that is being categorized. When the new observation is received, then the classifier can be used to categorize the new observation. Classifiers can be used for many analysis applications, including analysis of one or more faces. The use of classifiers can be the basis of analyzing the one or more faces for gender, ethnicity, and age; for detection of one or more faces in one or more videos; for detection of facial features, and so on. The observations can be analyzed based on one or more of a set of quantifiable properties. The properties can be described as features and explanatory variables and can include various data types that can include numerical (integer-valued, real-valued), ordinal, categorical, and so on. Some classifiers can be based on a comparison between an observation and prior observations as well as on functions such as a similarity function, a distance function, and so on.

Classification can be based on various types of algorithms, heuristics, codes, procedures, statistics, and so on. Many techniques exist for performing classification. For example, classification of one or more observations into one or more groups can be based on distributions of the data values, probabilities, and so on. Classifiers can be binary, multiclass, linear and so on. Algorithms for classification can be implemented using a variety of techniques including neural networks, kernel estimation, support vector machines, use of quadratic surfaces, and so on. Classification can be used in many application areas such as computer vision, speech and handwriting recognition, and so on. Classification can be used for biometric identification of one or more people in one or more frames of one or more videos.

Returning to FIG. 5, the detection of the second face can include identifying facial landmarks, generating a bounding box, and prediction of a bounding box and landmarks for a next frame, where the next frame can be one of a plurality of frames of a video containing faces. A first video frame 500 includes a boundary 510, a first face 512, and a second face 514. The frame 500 also includes a bounding box 520. Facial landmarks can be generated for the first face 512. Face detection can be performed to initialize a second set of locations for a second set of facial landmarks for a second face within the video. Facial landmarks in the video frame 500 can include the facial landmarks 522, 524, and 526. Facial landmarks can include corners of a mouth, corners of eyes, eyebrow corners, tip of nose, nostrils, chin, tips of ears, and so on. The performing of face detection on the second face can include performing facial landmark detection with the first frame from the video for the second face, and can include estimating a second rough bounding box for the second face based on the facial landmark detection. For example, the estimating of a second rough bounding box can include bounding box 520. Bounding boxes can also be estimated for one or more other faces within the frame 510. The bounding box can be refined, as can one or more facial landmarks. The refining of the second set of locations for the second set of facial landmarks can be based on localized information around the second set of facial landmarks. The bounding box 520 and the facial landmarks 522, 524, and 526 can be used to estimate future locations for the second set of locations for the second set of facial landmarks in a the future video frame from the first video frame.

A second frame 502 is also shown. The second video frame 502 includes a frame boundary 530, a first face 532, and a second face 534. The second frame 502 also includes a bounding box 540 and the facial landmarks 542, 544, and

546. In other embodiments, any number of facial landmarks can be generated and used for facial tracking of the two or more faces of a video frame such as the shown second video frame 502. Facial points from the first face can be distinguished from other facial points. In embodiments, the other facial points include facial points of one or more other faces. The facial points can correspond to the facial points of the second face. The distinguishing of the facial points of the first face and the facial points of the second face can be used to distinguish between the first face and the second face, to track either or both of the first face and the second face, and so on. Other facial points can correspond to the second face. As mentioned above, any number of facial points can be determined within a frame. One or more of the other facial points that are determined can correspond to a third face. The location of the bounding box 540 can be estimated, where the estimating can be based on the location of the generated bounding box 520 shown in the prior frame 500. The three facial points shown, 542, 544, and 546 might lie within the bounding box 540 or might not lie partially or completely within the bounding box 540. For example, the second face 534 might have moved between the first video frame 500 and the second video frame 502. Based on the accuracy of the estimating of the bounding box 540, a new estimation can be determined for a third, future frame from the video, and so on.

Figure 6:
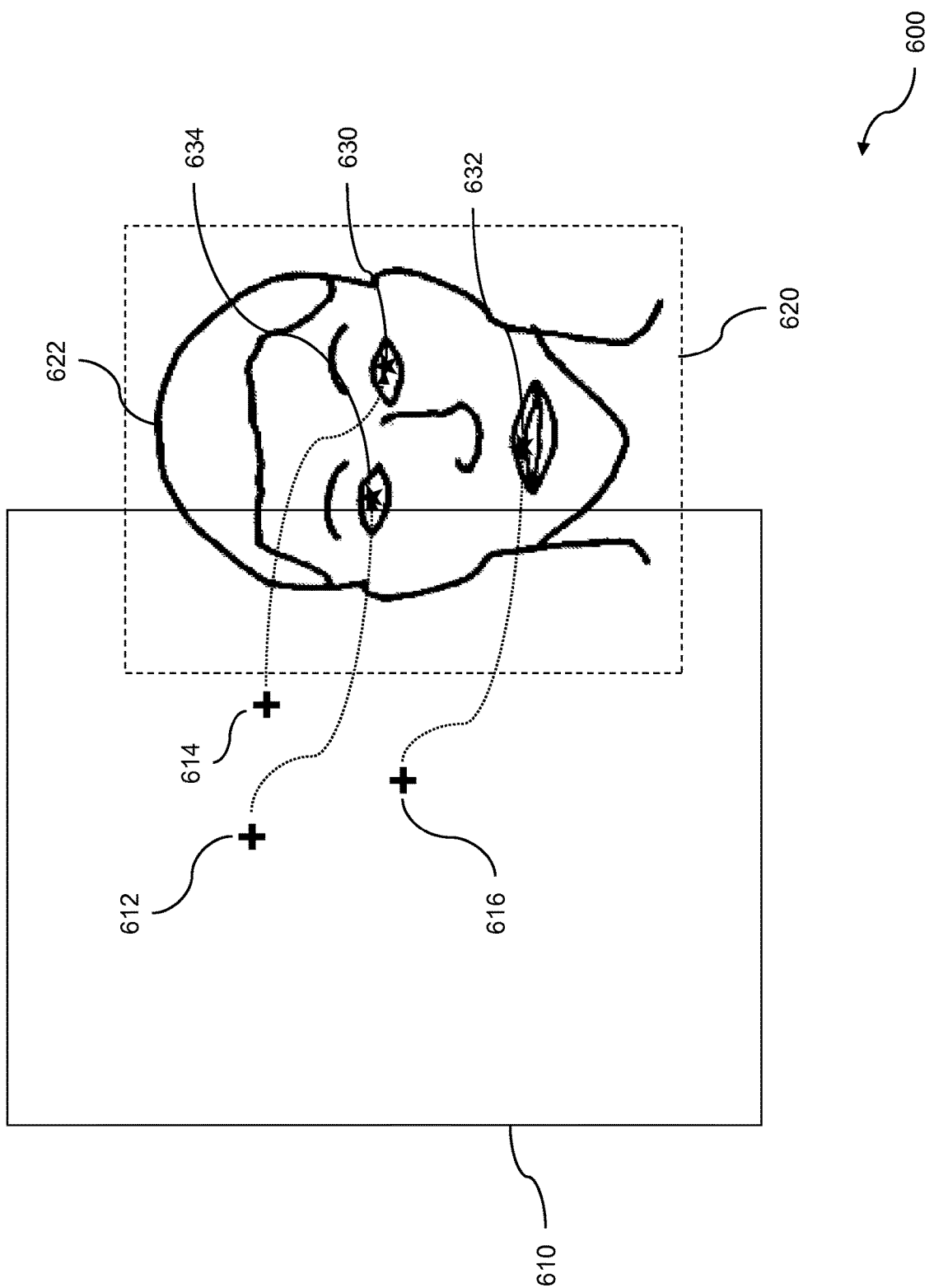
FIG. 6 is an example showing first and second bounding boxes.

FIG. 6 is an example showing first and second bounding boxes 600. As described above, a video that contains a face of a person can be captured using any appropriate image capture technique. The video can be partitioned into a plurality of frames, and face detection can be performed on a first frame and other frames from the plurality of frames from the video. The face detection can include performing facial landmark detection, facial point detection, distinguishing mark detection, and so on. In the case of facial landmark detection, the facial landmarks can include corners of a mouth, corners of eyes, eyebrow corners, tip of nose, nostrils, chin, tips of ears, etc. Any facial landmark that can be appropriate to facial detection can be included in the performing facial landmark detection. The result of the facial landmark detection can be any number of facial landmarks. In the example 600, three initial locations for facial landmarks are identified: the landmarks 612, 614, and 616. Based on the locations of the facial landmarks 612, 614, and 616, a bounding box 610 can be generated for the face within the first frame from the plurality of frames. The bounding box 610 can be a square, a rectangle, and/or any other appropriate geometric shape suited to the facial detection. The bounding box 610 can be a rough bounding box, a refined bounding box, an optimized bounding box, and so on. The bounding box 610 can be a minimum-dimension bounding box, where the minimized dimension can include area, volume, hyper-volume, and so on. The bounding box 610 can be generated based on analysis, calculation, detection, drawing, estimation, simulation, prediction, and so on. The bounding box 610 and the facial landmarks 612, 614, and 616 can be used to estimate future locations for facial landmarks in one or more future frames. The estimating of future locations of facial landmarks can be based on a velocity for one or more of the locations. That is, if the face or one or more facial landmarks is estimated to be moving for one video frame relative to another video frame, then the velocity of one or more of the facial landmarks can be used so that a given facial landmark can be estimated to move from a first location in the first frame to a second location in a second frame. The estimating of the future locations for the landmarks can be based on an angular velocity for one or more of the facial landmark locations. If the face is estimated to be rotating for one video frame relative to another video frame, then the angular velocity of one or more of the facial landmarks can be used so that a given facial landmark can be estimated to move from one location in the first frame to a second location in the second frame. As seen in the example 600, the face 622 is offset from the bounding box 610. A second set of facial landmarks 630, 632, and 634, can be found for the location of the face 622. The second set of facial landmarks 630, 632, 634 can be analyzed, calculated, detected, drawn, estimated, simulated, predicted, etc., for the current location within the frame of the face 622. A second bounding box 620 can be determined based on the location of the face 622. The second bounding box 620 can be a square, a rectangle, and/or any other appropriate geometric shape suited to the facial detection. The second bounding box 620 can be a rough bounding box, a refined bounding box, an optimized bounding box, and so on. The second bounding box 620 can be a minimum-dimension bounding box, where the dimension can include area, volume, hyper-volume, and so on. The second bounding box and the locations of the facial landmarks 630, 632, and 634 of the face 622 can be used to estimate future locations of facial points for a future frame from the video.

Figure 7:
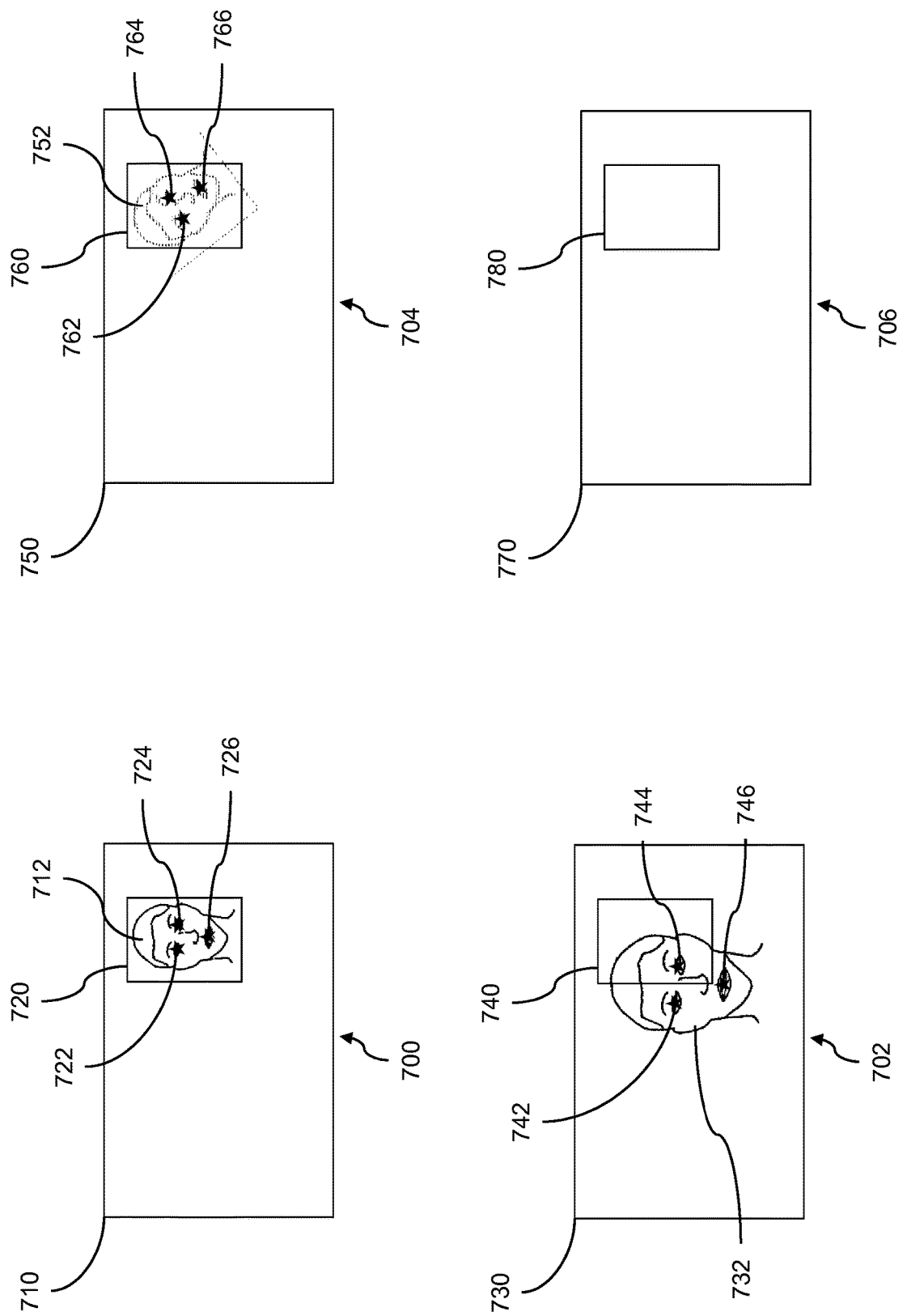
FIG. 7 illustrates frame processing for face translation, rotation, and no detection.

FIG. 7 illustrates frame processing for face translation, rotation, and no detection. A video that contains a face of a person can be captured using an image capture technique and can be partitioned into a plurality of frames. The frames from the video can then be analyzed for facial tracking of the person in the video. The face detection can be based on performing facial landmark detection, facial point detection, distinguishing mark detection, and any other technique appropriate to detection of a face. For facial landmark detection, the facial landmarks can include corners of a mouth, corners of eyes, eyebrow corners, tip of nose, nostrils, chin, or tips of ears, and so on. As before, any facial landmark that can be appropriate to facial detection can be included in the performing facial landmark detection, and the result of the facial landmark detection can be any number of facial landmarks. An initial frame 700 is shown with a frame boundary 710, a face 712, and the facial landmarks 722, 724, and 726. A bounding box 720 can be generated for the face within the first frame. The bounding box 720, including a rough bounding box, a refined bounding box, an optimized bounding box, a minimized bounding box and so on, can be estimated for the face 712 based on the detection of the facial landmarks 722, 724, and 726. Between frames of the video, the face of the person can appear to change. For example, the changes that can occur to the face can include rotation (around an X-axis, a Y-axis, and a Z-axis), translation, scaling (zoom in and zoom out), and no detection, the latter describing a situation where the face is no longer detectable in the frame. The frame 702 shows a frame boundary 730, a face 732, a bounding box 740, and the facial landmarks 742, 744, and 746. The location of the bounding box 740 is based on estimating a location based on the location of the face in a previous frame. Estimating future locations for the facial landmarks 742, 744, and 746 of the face 732 can be based on a velocity for one or more of the locations. Similarly, estimating of the location of the bounding box 740 and future locations of the bounding box can be based on the facial landmark detection and estimating future landmark locations. Returning to the frame 702, the face 732 can be translated and scaled up (zoom in) as shown in the frame. The frame 704 shows a frame boundary 750, a face 752, a bounding box 760, and the facial landmarks 762, 764, and 766. While the bounding box 760 is shown to partially or entirely surround the face 752, the face 752 can be rotated relative to a face in another frame. For example, the face 752 appears rotated relative to the face 712. The face 752 can be rotated by any amount, where the amount of rotation can be measured in degrees, radians, and so on. The rotation of the face 752 can be due to an angular velocity. Similar to using landmark velocity, the estimating of the future locations for the landmarks can be based on an angular velocity for one or more of the locations. The result of the rotation of the face 752 can be the generation of a new bounding box 760. The bounding box that is generated can be a square, a rectangle, and/or any other appropriate polygon for surrounding a shape with a frame. The new bounding box 760 can be used for future frames from the video. Continuing with the illustration, the frame 706 shows a frame boundary 770 and a bounding box 780. The location of the bounding box 780 is based on estimating a location for a face in the frame 706 based on the location of the face in a previous frame. In the case of the frame 706, no face is detected. The face that might have been detected in a previous frame might not be detected in the current frame because of a velocity of one or more landmarks, an angular velocity of one or more landmarks, and so on. Various algorithms, heuristics, and other techniques can be used to proceed to another frame using the present bounding box, to proceed to another frame to calculate a new bounding box for the new frame, and so on.

Figure 8:
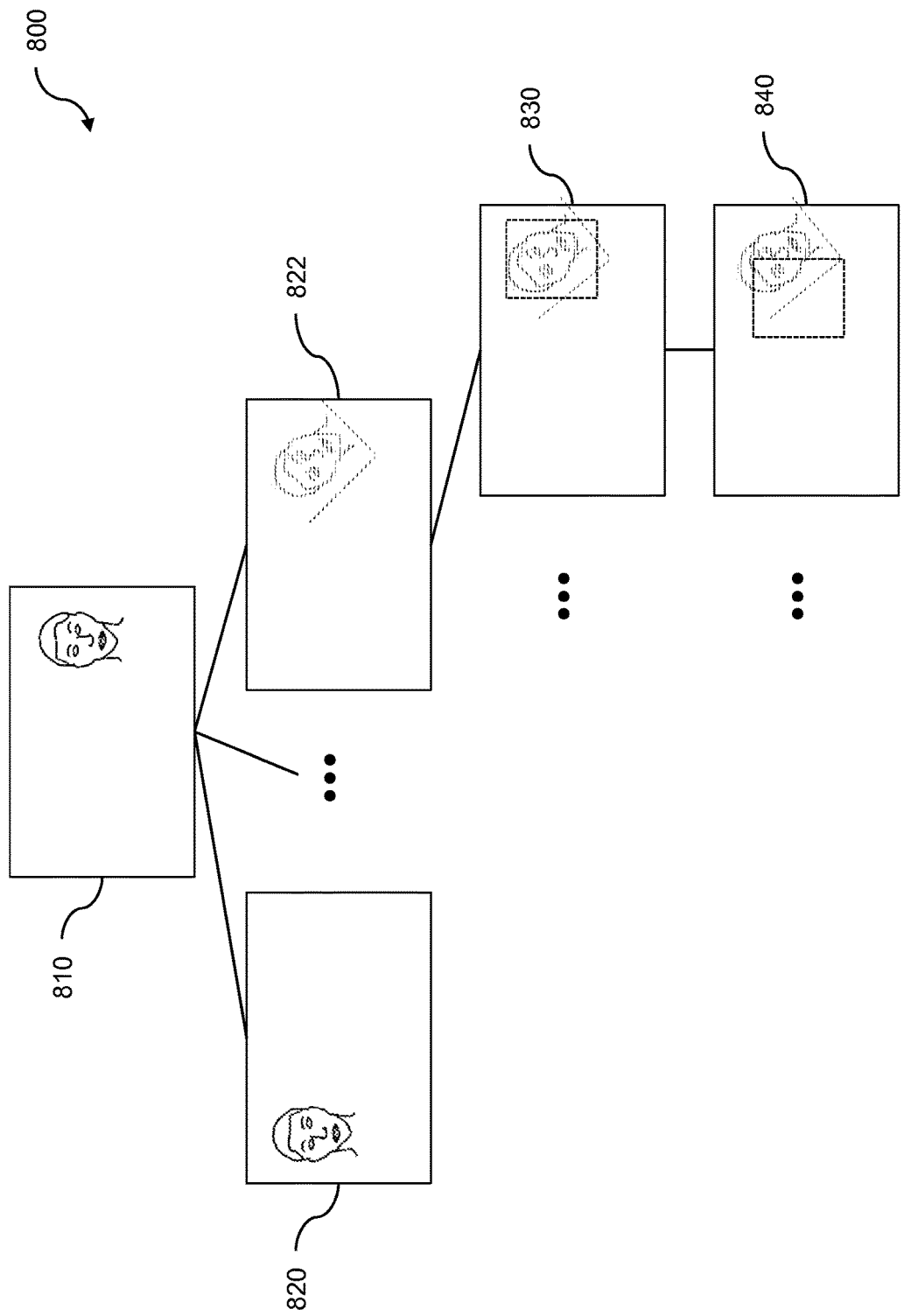
FIG. 8 is an example showing training.

FIG. 8 is an example showing training. The training shown in example 800 can include training one or more classifiers for a video clip for facial detection. As discussed above, a classifier can be an algorithm, heuristic, function, piece of code, etc., that can be used to identify into which of a set of categories a new or particular observation, sample, datum, etc. should be placed. The classifier can be trained, and the training of the one or more classifiers can be based on analyzing a known set of data known as a training set. The training set of data includes data for which category memberships of the data can be known, or supervised training. The supervised training can include training of classifiers for a machine learning technique. For example, a support vector machine (SVM) can use the classifier. When a training set of data is not available then unsupervised training of the one or more classifiers can be performed.

Various techniques can be used to train tracking facial landmarks of a face of a person, for example, and to improve the tracking of the facial landmarks. The tracking can include tracking facial points, distinguishing features, and so on. The training can include generating a mirror image of the face. The mirror image of the face can be generated, for example, by finding a centerline in the Z-axis for the face, and then rotating the face about the Z-axis. The training can include generating a scaled image of the face. The face can be enlarged (zoom-in), reduced (zoom-out), and so on. Any appropriate technique can be used for the training One example of facial training is shown in the example 800. The training can be based on automatic techniques, manual techniques, algorithms, heuristics, and so on. The training can be used to improve several aspects of facial tracking including detecting locations of one or more facial landmarks, refining of the location of the one or more facial landmarks, estimating locations of one or more facial landmarks in one or more future video frames, simulating an output of a facial detector, and so on. The training can begin with a video frame 810 which contains a face. Various adaptations can be made to the face in the video frame 810 including rotating, forming a mirror image, translating, removing, scaling, and so on. The frames 820 and 822 show variations of the frame 810 in which a mirror image is formed of the face in the frame 820, and the face is rotated in the frame 822. Many other adaptations can be made to the frame which contains the face, including translating the face north, south, east, or west within the frame, translating the face diagonally northwest, northeast, southeast, southwest, and so on. Noise can be introduced into the frames to improve training for detection. A bounding box can be determined for frames generated for variations of the face, such as the bounding box generated for a rotated face as shown in the frame 830. The training can include further variations of the video frame containing the face. For example, the frame 840 shows a bounding box determined for a previous frame being applied to the frame containing the rotated face. The bounding box in the frame 840 demonstrates a box translated from an original position for a face. The translation can be accomplished by shifting the bounding box, by shifting the frame, by shifting the face, and so on. The training technique or techniques can continue for various faces, for numbers of faces partially or completely within a frame, for various degrees of rotation, for various distances and directions of translation, and so on. Additional training techniques can be used individually and combined with other training techniques. The translating of the bounding box to a different location as shown in the frame 840 can be based on velocity of one or more facial landmarks that are determined, angular velocity of one or more facial landmarks that are determined, and so on.

Figure 9:
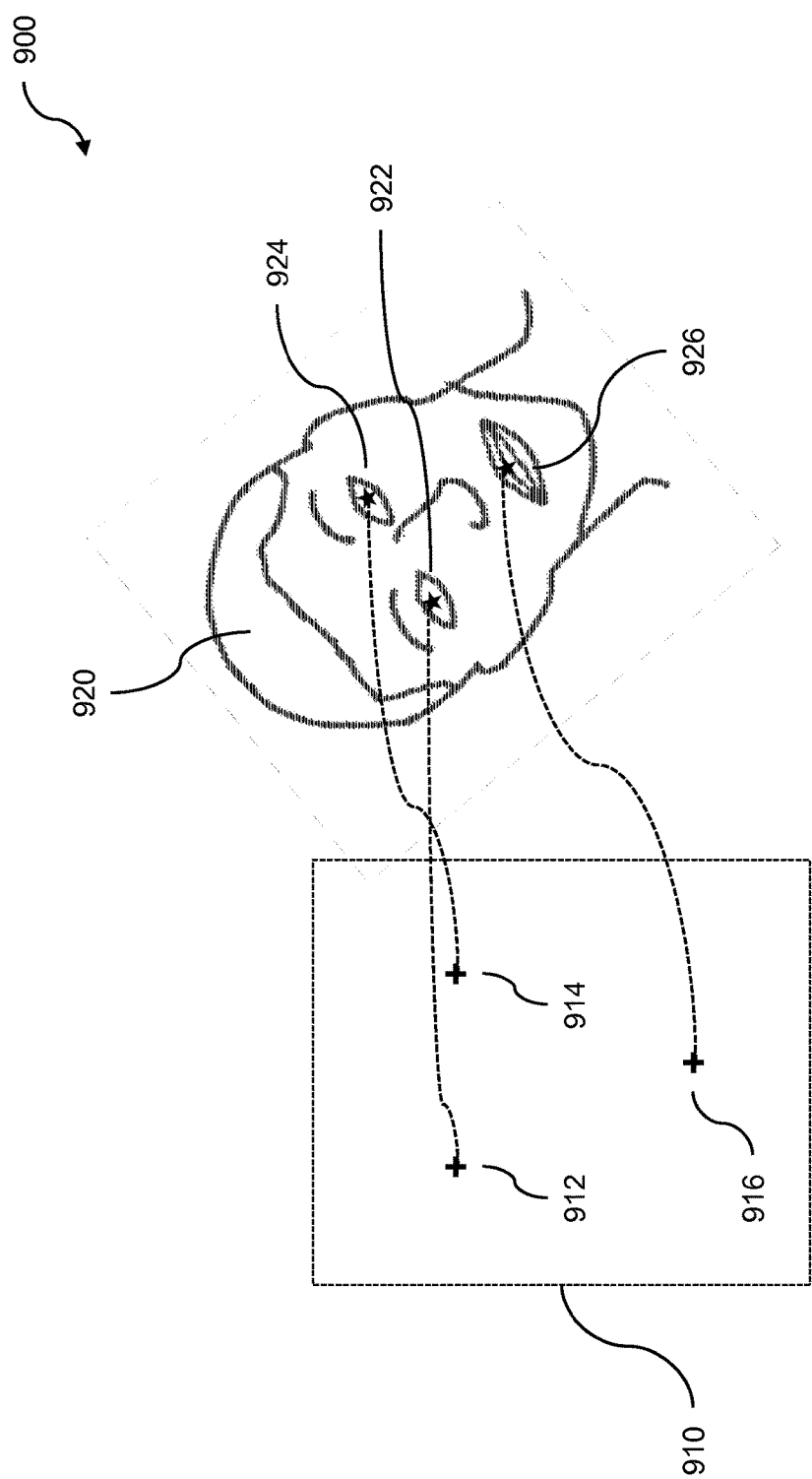
FIG. 9 shows example displacement of learned points.

FIG. 9 shows example displacement of learned points 900. The displacement of learned points can be based on analysis of a video which contains a face. The video which contains a face of a person, for example, can be captured using any appropriate image capture technique. The video can be partitioned into a plurality of frames, and face detection can be performed for any of the frames from the plurality of frames from the video. The face detection can include performing facial landmark detection, facial point detection, distinguishing mark detection, etc. For facial landmark detection, the facial landmarks can include corners of a mouth, corners of eyes, eyebrow corners, tip of nose, nostrils, chin, tips of ears, etc. Any facial landmark that can be appropriate to facial detection can be included in the performing facial landmark detection. The result of the facial landmark detection can be any number of facial landmarks. A frame from the plurality of frames partitioned from the captured video can be analyzed, and a bounding box and facial features can be identified for the frame. An example bounding box 910 along with example facial points 912, 914, and 916 can be generated. The bounding box 910 and the facial points 912, 914 and 916 can be identified using manual techniques; automatic techniques; hybrid techniques; a combination of manual, automatic, and hybrid techniques; algorithms; heuristics; and so on. The bounding box 910 and the facial points 912, 914, and 916 can be learned and can be used for facial tracking in future frames of a video. Facial tracking in future frames can be estimated, where the estimating of the future locations for the landmarks can be based on a velocity for one or more of the locations. That is, the velocity of one or more of the determined facial landmarks can be calculated, and the one or more velocities can be used for the estimating. Similarly, the estimating of the future locations for the landmarks can be based on an angular velocity for one or more of the locations. One or more of the determined facial landmarks can be rotating, and the angular velocity of the rotating can be used for the estimating. For example, the facial points 912, 914, and 916 can be displaced to the points 922, 924, and 926, respectively, for the face 920. The displacement can be caused by translation, rotation, generating a mirror image, and so on. The learning of points which are displaced can be used to improve the estimating of future locations of facial points and bounding boxes for future frames.

Figure 10:
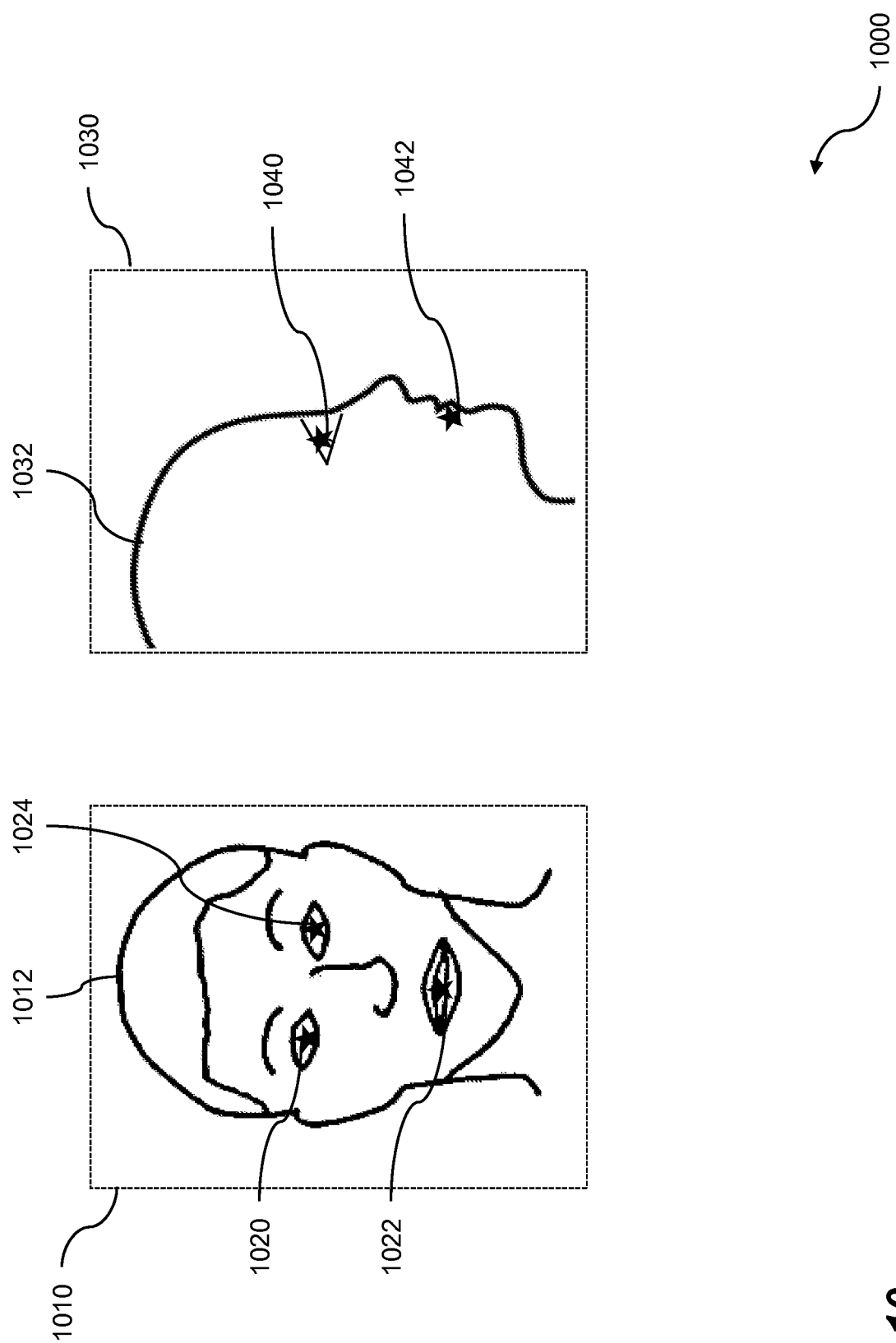
FIG. 10 shows example training using rotation mapping around the z-axis.

FIG. 10 shows example training using rotation mapping around the z-axis 1000. Facial tracking techniques as described above address tracking faces, which can vary from frame to frame of a video with respect to scale, translation, rotation and so on. The facial techniques can have a substantially similar percentage of the face in common from frame to frame. For example, a face which can be viewed full-on in one frame can be viewed as rotated and full-on in a later frame. The face can also rotate around the z-axis such that a face can be viewed full-on in one frame and can be viewed in profile in a later frame, for example. This latter learning for facial tracking can include learning to map locations of facial landmarks, facial points, facial characteristics, distinguishing marks, and so on, in a first frame to a bounding box of a second frame. The example 1000 illustrates a face 1012 for which a bounding box 1010 and locations for the facial landmarks 1020, 1022, and 1024 have been determined. The determining of the bounding box and locations for facial landmarks can include automatic techniques, manual techniques, hybrid techniques, and so on. The face 1012 can be rotated about the z-axis and can generate a face in profile 1032. A bounding box 1030 and locations for the facial landmarks 1040 and 1042 can be determined. Notice that some facial landmarks that can be evident in the first bounding box may not be visible and/or detectable in the second bounding box. For example, facial landmark 1024 can be visible in the first bounding box 1010 and not be visible in the second bounding box 1030. The learning can include mapping of the x-y coordinates (locations) of the facial landmarks to the coordinates of the bounding box 1030. The bounding box 1030 can be delineated by determining the top-left x-y coordinates and bottom-right x-y coordinates of the bounding box. While a bounding box has been described, any other appropriate polygon could be used to form a boundary around a face including a square, a rectangle, and/or other more complex polygons.

Figure 11:
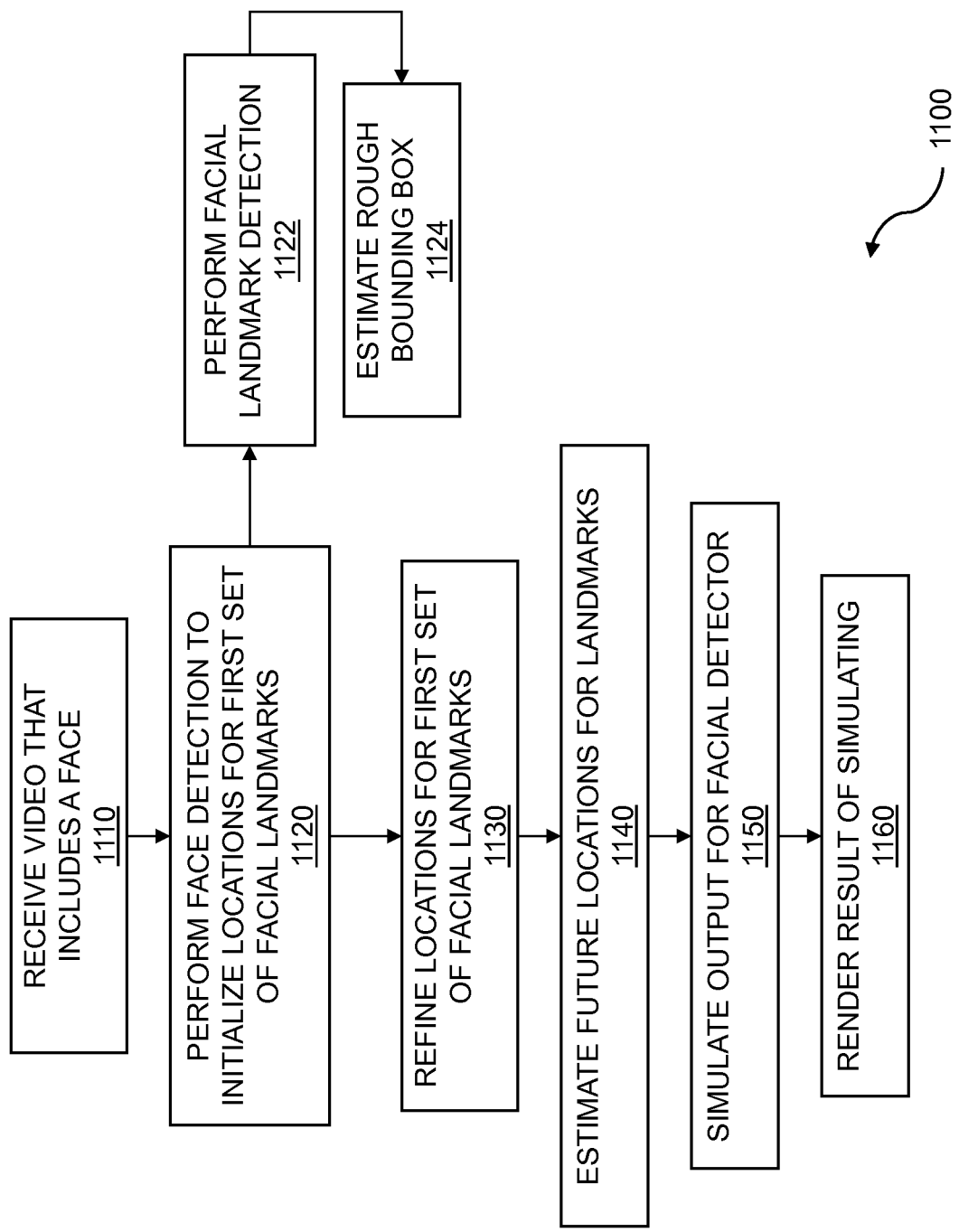
FIG. 11 is a flow diagram for facial tracking from a server perspective.

FIG. 11 is a flow diagram for facial tracking from a server perspective. The flow 1100 describes a computer-implemented method for facial detection. The flow 1100 includes receiving a video that includes a face 1110. The video that is received can include more than one face. The flow 1100 includes performing face detection to initialize locations for a first set of facial landmarks 1120 within a first frame from the video. The initializing locations can include performing facial point detection, detecting distinguishing marks, and so on. The flow 1100 includes performing facial landmark detection 1122 within the first frame from the video. The face that can be detected can be any size within the first frame from the video. The face can be rotated by any amount relative to an X-axis. For example, the face can be rotated by zero degrees (straight up and down), rotated by 15 degrees left, 10 degrees right, and so on. The face can be rotated by any amount relative to a Z-axis. For example, the face can be detected straight on, in three-quarter profile, in profile, in one-quarter profile, and so on. The flow 1100 includes estimating a rough bounding box 1124 for the face based on the facial landmark detection. The bounding box can be a rectangle, a square, or any other geometric shape appropriate to the facial detection. The estimating of the bounding box can be based on box area, box volume, box hyper-volume, and so on. The flow 1100 includes refining the locations for the first set of facial landmarks 1130 based on localized information around the facial landmarks. For example, the refining the first set of facial landmarks can include centering location points on the facial landmarks. The facial landmarks can include corners of a mouth, corners of eyes, eyebrow corners, tip of nose, nostrils, chin, tips of ears, and so on. The flow 1100 includes estimating future locations for the facial landmarks 1140 for a future frame from the first. The estimating future locations can include using the locations of facial points, facial landmarks, facial characteristics, distinguishing marks, etc. in a first frame to estimate the locations of facial points, facial landmarks, facial characteristics, distinguishing marks, etc. in a second frame, for example. The flow 1100 includes simulating an output for a facial detector 1150 based on the estimating of the future locations for the facial landmarks. The output of a facial detector can be simulated based on the estimated locations of the future facial points. The simulating of the facial detector can generate an output, where the output can include a bounding box for the face, for example. The flow 1100 includes rendering a result of the simulating the output 1160 for the facial detector. The output for the facial detector can be rendered on a computer screen, a smartphone display, a tablet display, a projector, and so on. Any display appropriate to the rendering of the output of the facial detector can be used. Various steps in the flow 1100 may be changed in order, repeated, omitted, or the like without departing from the disclosed concepts. Various embodiments of the flow 1100 may be included in a computer program product embodied in a non-transitory computer readable medium that includes code executable by one or more processors.

Figure 12:
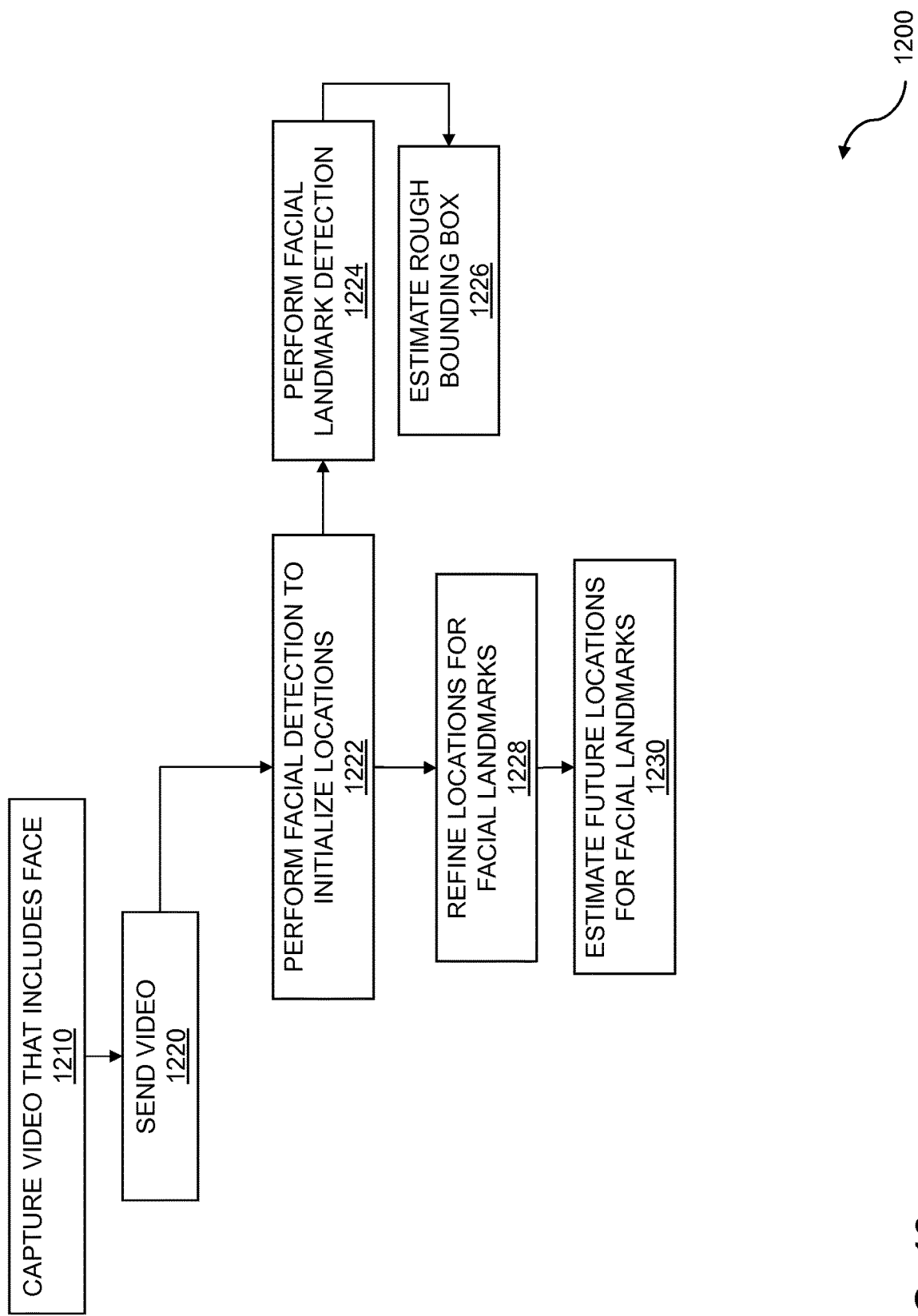
FIG. 12 is a flow diagram for facial tracking from a device perspective.

FIG. 12 is a flow diagram for facial tracking from a device perspective. The flow 1200 describes a computer-implemented method for facial detection. The facial tracking can take place on any electronic device including a computer, a laptop computer, a smartphone, a PDA, a tablet computer, and so on. The flow 1200 includes capturing a video that includes a face 1210. The videos can be captured using a camera, where the camera can include a video camera, still camera, thermal imager, CCD device, phone camera, three-dimensional camera, depth camera, light field camera, multiple webcams used to show different views of a person, or any other type of image capture apparatus that can allow captured data to be used in an electronic system. The camera can be coupled to a personal electronic device including a laptop computer, a smartphone, a PDA, a tablet computer, etc. The flow 1200 includes sending the video 1220 which can be sent to another device, a plurality of devices, a server, and so on. The video can be sent for a variety of facial tracking and other analyses. The flow 1200 includes sending the video to perform face detection to initialize locations 1222 for a first set of facial landmarks within a first frame from the video. The facial landmarks can include corners of a mouth, corners of eyes, eyebrow corners, tip of nose, nostrils, chin, tips of ears, and so on. The flow 1200 includes performing facial landmark detection 1224 within the first frame from the video. Any number of facial landmarks can be included in the detection. The detection can also include detecting facial points, distinguishing marking and characteristics, and so on. The flow 1200 includes estimating a rough bounding box 1226 for the face based on the facial landmark detection. As described above, the bounding box can be a square, a rectangle, or any other geometric shape suitable to facial detection. The flow 1200 includes sending the video to refine the locations for the first set of facial landmarks 1228 based on localized information around the first set of facial landmarks. The refining the first set of facial landmarks can include centering location points on the facial landmarks on the facial landmarks, for example. The flow 1200 includes sending the video to estimate future locations for landmarks 1230 within the first set of facial landmarks for a future frame from the first frame. The estimating future locations can include using the locations of facial points, facial landmarks, facial characteristics, distinguishing marks, etc. in a first frame to estimate the locations of facial points, facial landmarks, facial characteristics, distinguishing marks, etc. in a second frame, for example. Various steps in the flow 1200 may be changed in order, repeated, omitted, or the like without departing from the disclosed concepts. Various embodiments of the flow 1200 may be included in a computer program product embodied in a non-transitory computer readable medium that includes code executable by one or more processors.

Figure 13:
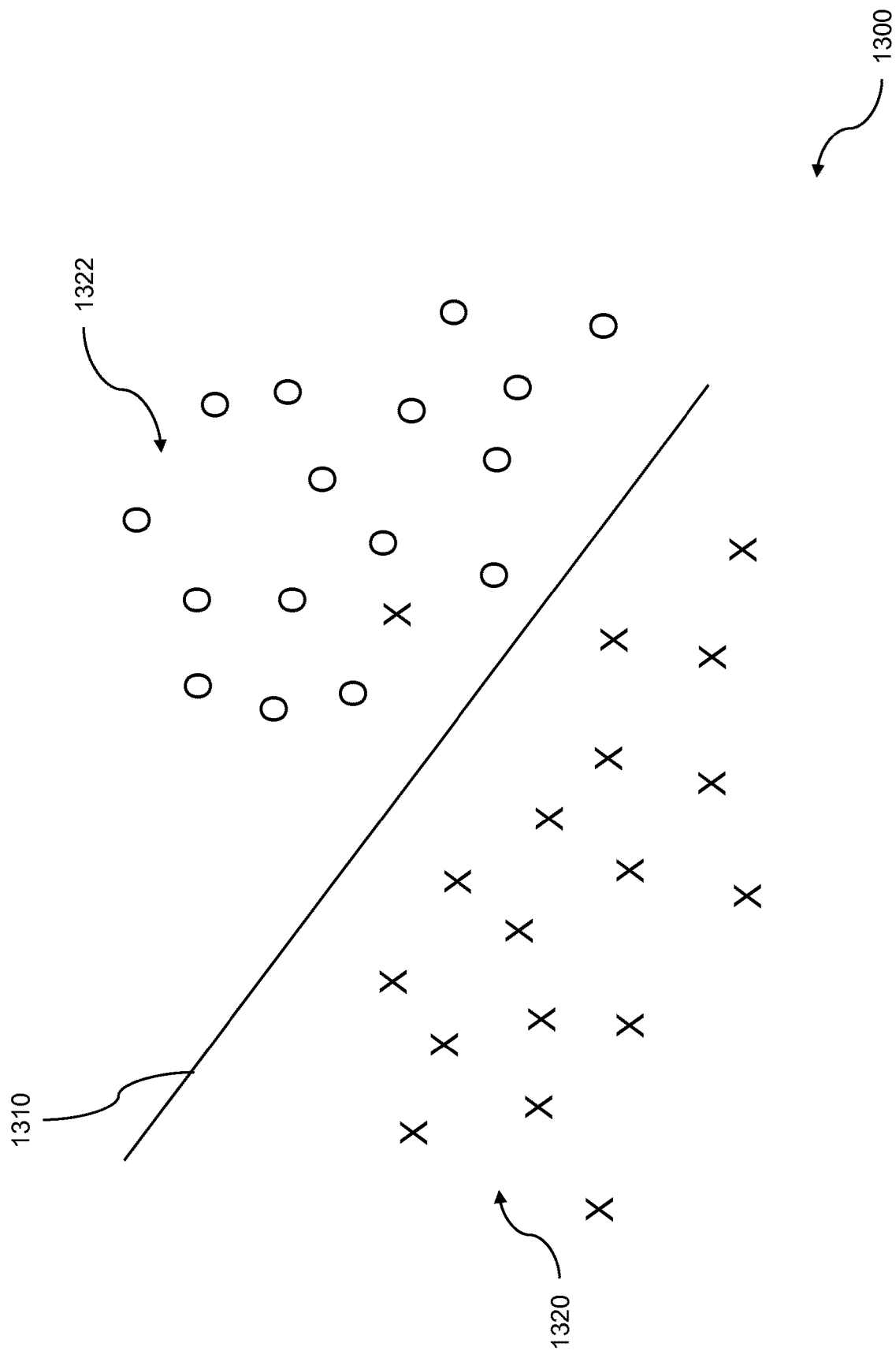
FIG. 13 is an example showing linearly separable data.

FIG. 13 is an example showing linearly separable data 1300. Videos can be collected from a plurality of people. The videos, which can contain facial data, mental state data, emotional state data, physiological data, and so on, can be partitioned for analysis. The video data can be analyzed for a variety of purposes including identifying facial expressions, determining mental states, and so on. The videos can be partitioned into frames, video clips, slideshows, and so on. Based on the analysis of the videos, various classifiers can be associated with the analysis data. The video data, the analysis data, the classifiers, etc., can be plotted as linearly separable data 1300. The plotted data can be identified, categorized, organized, etc., by a variety of qualifiers. For example, the linearly separable data 1300 can be qualified as data type X 1320, data type O 1322, and so on. A qualifier can be used to separate the plotted data. The separation technique can be based on a linear function and can be used for data which is identified as linearly separable. A line 1310 shows an example linear separation of the data types X 1320 and O 1322. Note that the separation by data type can completely separate the plurality of data types or can separate a majority of the data types. For example, there is one X which appears above the line 1310, while all of the remaining X's are clustered together below the line 1310.

Figure 14:
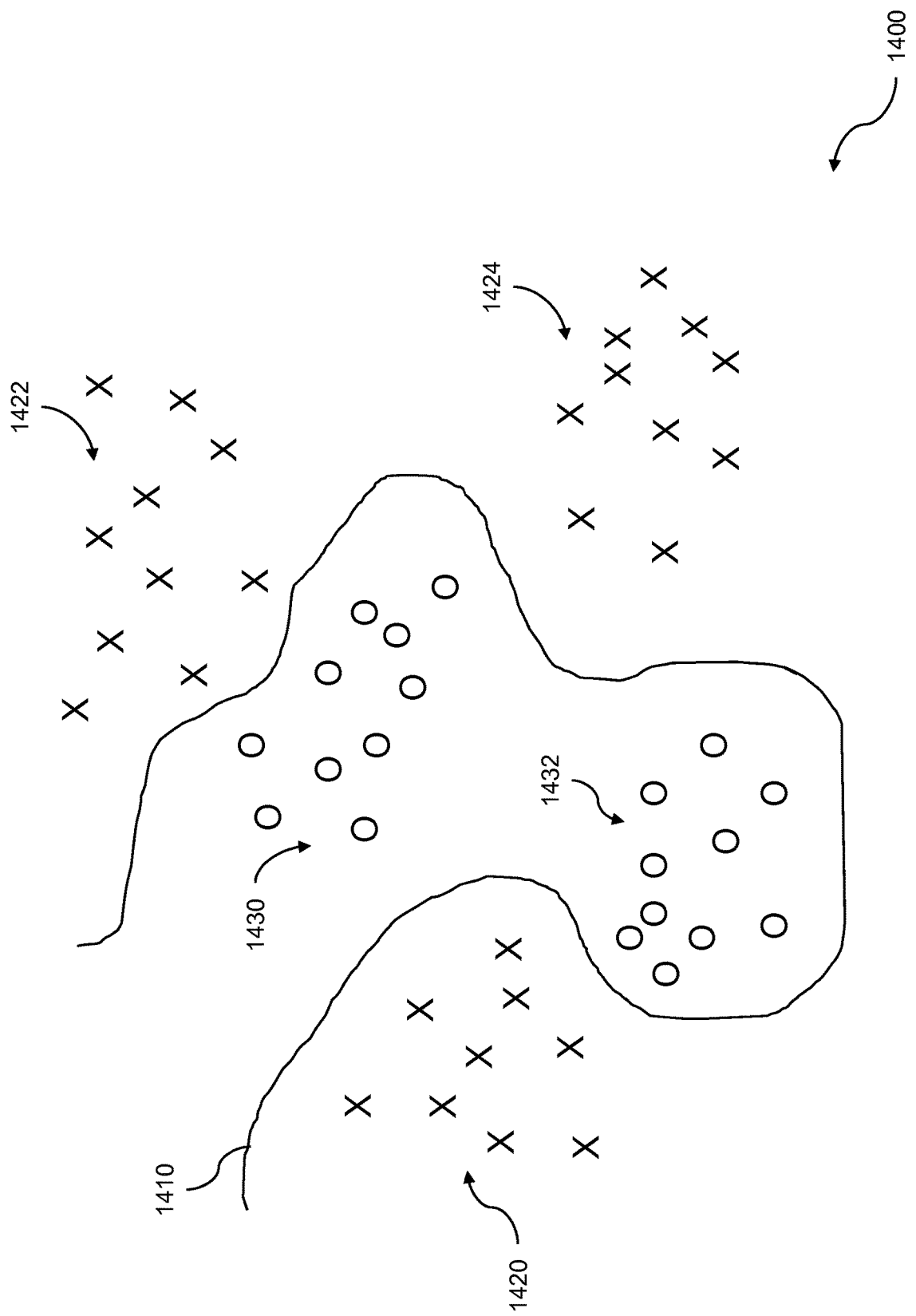
FIG. 14 is an example showing nonlinearly separable data.

FIG. 14 is an example showing nonlinearly separable data 1400. As in the case for linearly separable data as described above in FIG. 13, videos can be collected from a plurality of people. The videos, which can contain facial data, physiological data, etc., can be partitioned into frames. The video data can be analyzed for a variety of purposes, and can be partitioned into frames, video clips, slideshows, and so on. Based on the analysis of the videos, various classifiers can be associated with the analysis data. The video data, the analysis data, the classifiers, etc., can be plotted as nonlinearly separable data 1400 and clusters can appear in the plotted data. The plotted data can be identified by a variety of qualifiers. For example, the plotted data 1400 can be qualified as data type X 1420, 1422, and 1424; data type O 1430 and 1432; and so on. As in the case of linearly separable data as described above, the qualifier can be used to separate the plotted data. Unlike the linearly separable data as shown in FIG. 13, the plurality of clusters shown in example 1400 cannot be easily separated with a linear separation technique. In embodiments, the clustering is from a high dimensional perspective. A nonlinear technique can be used to partition the clusters by qualifier, type, and so on. A line 1410 shows an example nonlinear separation of the data types X and O by partitioning the data into clusters by data type X 1420, 1422, and 1424, and data type O 1430 and 1432.

In embodiments, an X can represent a positive case such as a smile while an O can represent a negative case, such as the lack of a smile. The lack of a smile can be a neutral face, a frown, or various other non-smile expressions. In other embodiments, frowns can be a cluster while neutral faces can be another cluster, for example. A non-linear classifier such as a support vector machine (SVM) can be used to analyze the data. A radial basis function (RBF) kernel can be employed. However, the SVM and RBF usage typically does not scale well as data sets become larger. Thus, in embodiments, a Nystrom method can be used to approximate RBF usage, resulting in analysis of the data that is better than using linear SVM analysis and faster than using RBF analysis.

Figure 15:
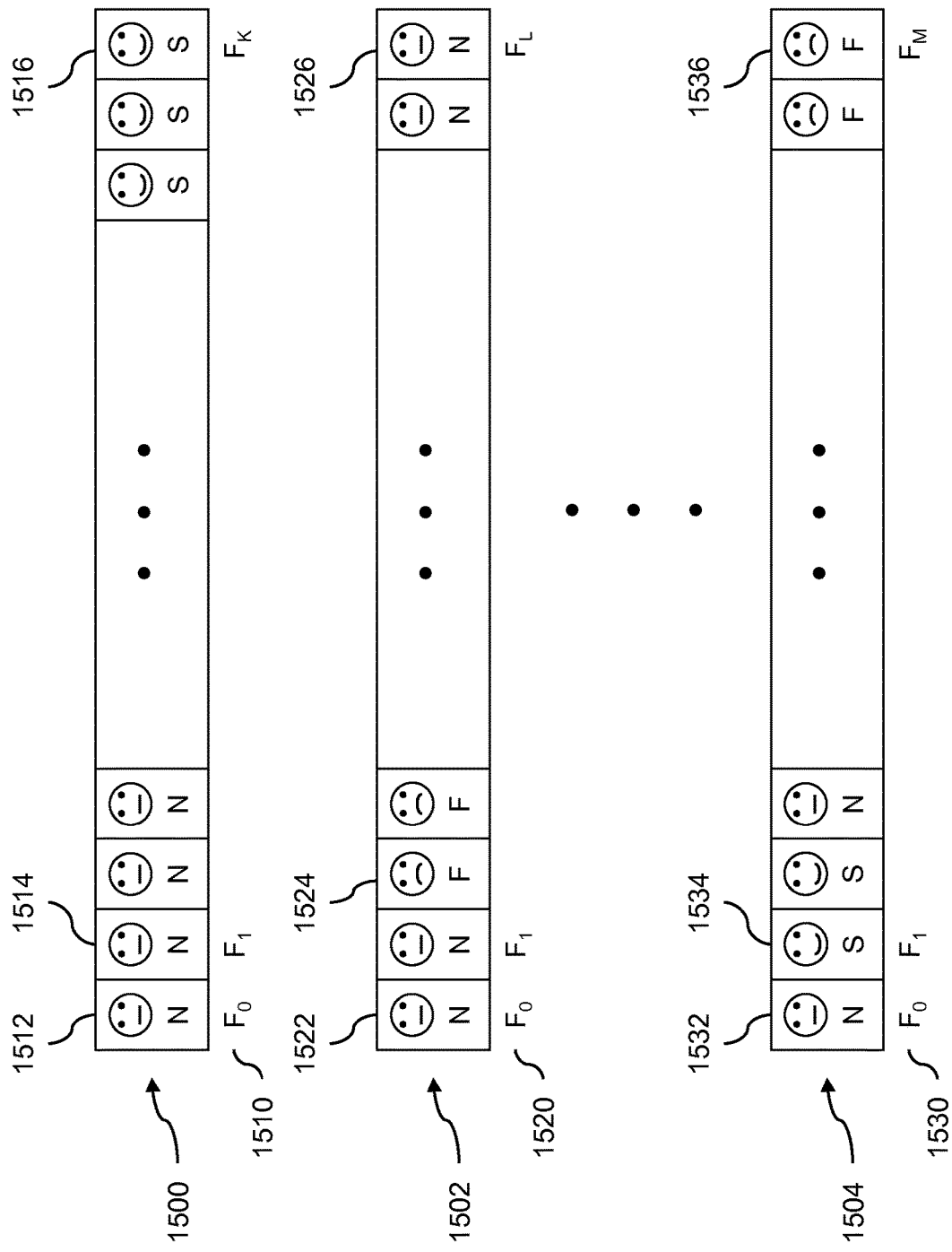
FIG. 15 shows example videos of people.

FIG. 15 shows example videos of people. The videos 1500, 1502, and 1504 can include a face of a person. The videos can be captured using a camera, where the camera can include a video camera, still camera, thermal imager, CCD device, phone camera, three-dimensional camera, depth camera, light field camera, multiple webcams used to show different views of a person, or any other type of image capture apparatus that can allow captured data to be used in an electronic system. The videos 1500, 1502, and 1504 of people can be partitioned into frames. The video 1500 can be partitioned into a series of frames 1510, the video 1502 can be partitioned into a series of frames 1520, and the video 1504 can be partitioned into a series of frames 1530. The individual frames can be labeled $F_0$, $F_1$, and so on up to $F_K$ for the video 1500; $F_0$, $F_1$, and so on up to $F_L$ for the video 1502; and $F_0$, $F_1$ and so on up to $F_M$ for the video 1504. In practice, any number of videos can be partitioned into any number of frames. The frames from the videos can be analyzed for the appearance of faces. The faces detected within the frames can in turn be analyzed for facial expressions. The facial expressions can include a smile, a neutral expression, a frown, and so on. The frames of the video 1500 can be analyzed for facial expressions to find a neutral expression 1512, a neutral expression 1514, a smile 1516, and so on. The frames of the video 1502 can be analyzed for facial expressions to find a neutral expression 1522, a frown 1524, a neutral expression 1526, and so on. The frames of the video 1504 can be analyzed for facial expressions to find a neutral expression 1532, a smile 1534, a frown 1536, and so on. The results of analyzing the videos 1500, 1502, and 1504 can be used to analyze an individual in a video, to identify trends within a video, to correlate reactions of people in different videos, and so on. The results of the analysis of the videos can be used for a variety of purposes including identifying the person or people in the videos, identifying any commonality of the facial expressions across a plurality of videos, and so on. The facial expressions can remain the same from frame to frame or can change from frame to frame.

In embodiments, a very large number of frames are obtained for various videos. A sample can be taken from these frames to approximate RBF-type analysis. The sampling can be random. In other cases, the sample can factor in context. For example, a most significant expression can be selected, such as picking a smile with the highest magnitude. In some situations, a large number of frames that are more relevant to the analysis can be selected from one person while include few or no frames of a video from another person. Based on this frame sampling and using Nystrom approximation, non-linear analysis of facial expressions can be accomplished.

Figure 16:
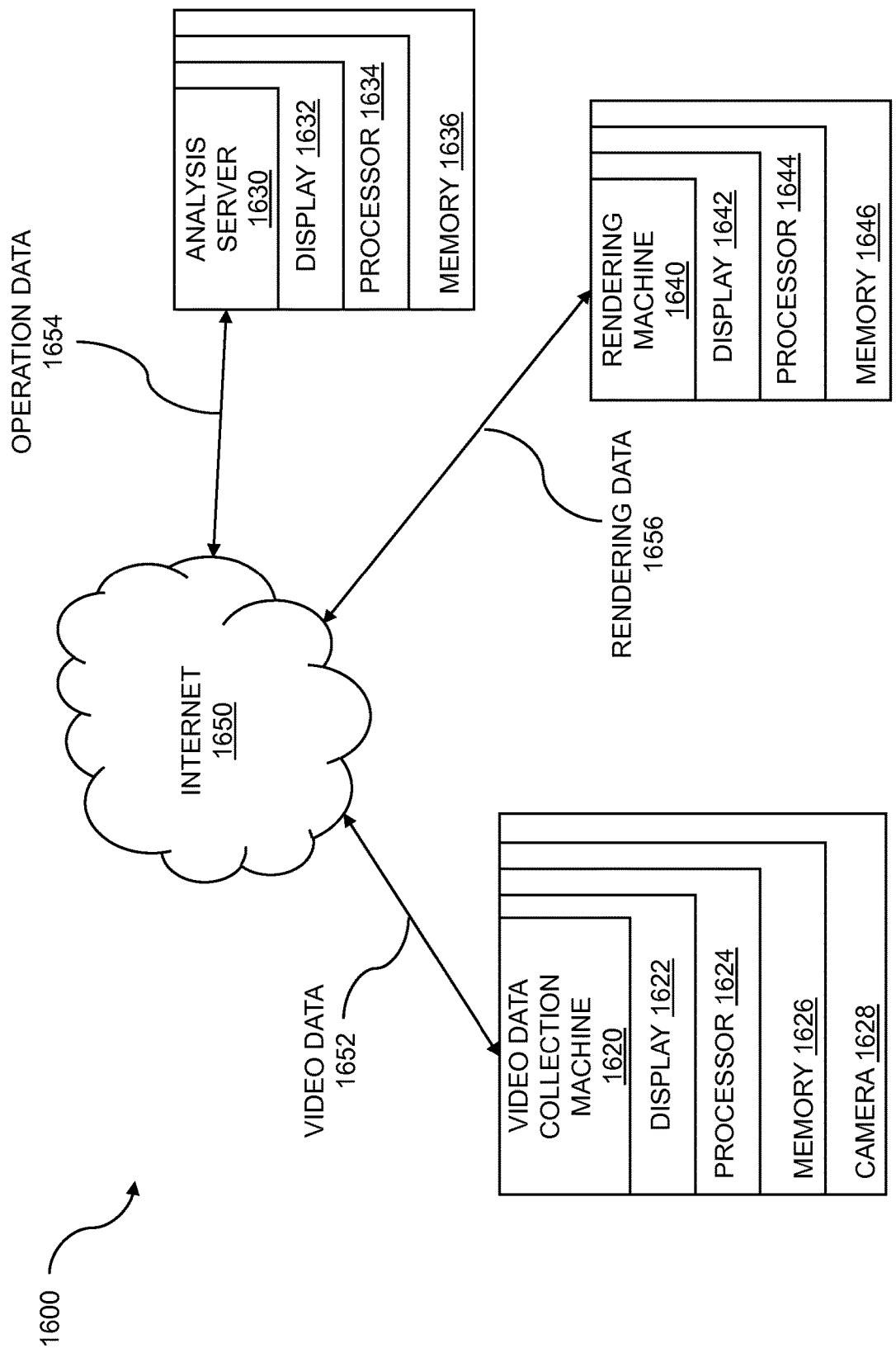
FIG. 16 is a system for facial tracking using classifiers.

FIG. 16 is a system for facial tracking using classifiers. The diagram illustrates an example system 1600 for video data collection, analysis, and rendering. This system 1600 can be used for facial tracking. The system 1600 can include one or more client machines or video data collection machines or devices 1620 linked to an analysis server 1630 via the Internet 1650 or another computer network. The video data collection machine 1620 comprises one or more processors 1624 coupled to a memory 1626 which can store and retrieve instructions, a display 1622, and a camera 1628. The memory 1626 can be used for storing instructions, facial data, videos, facial analysis, locations of facial points, and so on. The display 1622 can be any electronic display, including but not limited to, a computer display, a laptop screen, a net-book screen, a tablet computer screen, a surface computer screen, a smart phone display, a mobile device display, a remote with a display, a television, a projector, or the like. The camera 1628 can comprise a video camera, still camera, thermal imager, CCD device, phone camera, three-dimensional camera, depth camera, light field camera, multiple webcams used to show different views of a person, or any other type of image capture apparatus that can allow captured data to be used in an electronic system. The processor(s) 1624 of the video data collection machine 1620 are configured to receive facial data from people, and in some cases to analyze the facial data to detect locations of facial points. The facial data and locations of facial points data can be output in real time (or near real time), based on facial data captured using the camera 1628. In other embodiments, the processor(s) 1624 of the video data collection machine 1620 are configured to receive facial data from one or more people, analyze the facial data to detect locations of facial points, and send the video data 1652 to the analysis server 1630.

The analysis server 1630 can comprise one or more processors 1634 coupled to a memory 1636 which can store and retrieve instructions, and a display 1632. The analysis server 1630 can receive video data and can analyze the video data to detect locations of facial points and to simulate facial detection. The analysis of the facial data and the detection of the facial points can be performed by a web service and/or using cloud computing techniques. The analysis server 1630 can receive facial data or video data from the video data collection machine 1620. The analysis server can receive operation data 1654, where the operation data can include facial point detection data. The facial point detection data and other data and information related to facial tracking and analysis of the facial data can be considered video data 1652 and can be transmitted to and from the analysis server 1630 using the internet or another type of network. In some embodiments, the analysis server 1630 receives video data and/or facial data from a plurality of client machines and aggregates the facial data. The analysis server can perform facial tracking using classifiers.

In some embodiments, a displayed rendering of facial data and locations of facial points can occur on a different computer from the video data collection machine 1620 or the analysis server 1630. This computer can be termed a rendering machine 1640 and can receive facial tracking rendering data 1656, facial data, simulated facial detector data, video data, detected facial points data, and graphical display information. In embodiments, the rendering machine 1640 comprises one or more processors 1644 coupled to a memory 1646 which can store and retrieve instructions, and a display 1642. The rendering can be any visual, auditory, tactile, or other communication to one or more individuals. The rendering can include an email message, a text message, a tone, an electrical pulse, a vibration, or the like. The system 1600 can include a computer program product embodied in a non-transitory computer readable medium for mental state analysis comprising: code for obtaining a video that includes a face; code for performing face detection to initialize locations for a first set of facial landmarks within a first frame from the video wherein the face detection comprises: performing facial landmark detection within the first frame from the video; and estimating a rough bounding box for the face based on the facial landmark detection; code for refining the locations for the first set of facial landmarks based on localized information around the first set of facial landmarks; and code for estimating future locations for landmarks within the first set of facial landmarks for a future frame from the first frame.

Each of the above methods may be executed on one or more processors on one or more computer systems. Embodiments may include various forms of distributed computing, client/server computing, and cloud based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system" may be implemented by computer program instructions, by special-purpose hardware-based computer systems, by combinations of special purpose hardware and computer instructions, by combinations of general purpose hardware and computer instructions, and so on.

A programmable apparatus which executes any of the above mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are neither limited to conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the forgoing examples should not limit the spirit and scope of the present invention; rather it should be understood in the broadest sense allowable by law.

What is claimed is:

1. A computer-implemented method for facial detection comprising:
    obtaining a video that includes a face;
    performing face detection to initialize locations for a first set of facial landmarks within a first frame from the video containing an image of the face wherein the face detection comprises:
        performing facial landmark detection within the first frame from the video; and
        estimating a rough bounding box for the face based on the facial landmark detection;
    refining the locations for the first set of facial landmarks based on localized information around the first set of facial landmarks;
    estimating future locations for landmarks within the first set of facial landmarks for a future frame from the first frame; and
    training a classifier for a video clip for facial detection, wherein the training includes generating a scaled version of the image of the face directly from an initial frame, wherein the video is a chronological series of frames and the initial frame is an earliest frame containing the face in the chronological series of frames.

2. The method of claim 1 wherein the estimating of the future locations for the landmarks is based on a velocity for one or more of the locations.

3. The method of claim 1 wherein the estimating of the future locations for the landmarks is based on an angular velocity for one or more of the locations.

4. The method of claim 1 further comprising providing an output for a facial detector based on the estimating of the future locations for the landmarks.

5. The method of claim 1 further comprising performing face detection to initialize a second set of locations for a second set of facial landmarks for a second face within the video.

6. The method of claim 5 wherein the performing face detection on the second face comprises:
    performing facial landmark detection within the first frame from the video for the second face; and
    estimating a second rough bounding box for the second face based on the facial landmark detection.

7. The method of claim 6 further comprising refining the second set of locations for the second set of facial landmarks based on localized information around the second set of facial landmarks.

8. The method of claim 7 further comprising estimating future locations for the second set of locations for the second set of facial landmarks for the future frame from the first frame.

9. The method of claim 6 further comprising distinguishing facial points from the first face from other facial points.

10. The method of claim 9 wherein the other facial points correspond to the second face.

11. The method of claim 9 wherein one or more of the other facial points correspond to a third face.

12. The method of claim 1 further comprising analyzing the face using a plurality of classifiers.

13. The method of claim 12 wherein the plurality of classifiers provides for analysis of gender, ethnicity, or age corresponding to the face.

14. The method of claim 1 further comprising generating a bounding box for the face within the first frame.

15. The method of claim 1 wherein the training includes generating a mirror image of the face.

16. The method of claim 1 wherein the training includes generating a rotated image of the face.

17. The method of claim 1 wherein the training includes translating the bounding box to a different location.

18. The method of claim 1 further comprising evaluating the face to determine rotation about a z-axis of the face.

19. The method of claim 1 further comprising estimating a quality of the bounding box for the future frame.

20. A computer program product embodied in a non-transitory computer readable medium for facial detection comprising:
   code for obtaining a video that includes a face;
   code for performing face detection to initialize locations for a first set of facial landmarks within a first frame from the video containing an image of the face wherein the face detection comprises:
      performing facial landmark detection within the first frame from the video; and
      estimating a rough bounding box for the face based on the facial landmark detection;
   code for refining the locations for the first set of facial landmarks based on localized information around the first set of facial landmarks;
   code for estimating future locations for landmarks within the first set of facial landmarks for a future frame from the first frame; and
   code for training a classifier for a video clip for facial detection, wherein the training includes generating a scaled version of the image of the face directly from an initial frame, wherein the video is a chronological series of frames and the initial frame is an earliest frame containing the face in the chronological series of frames.

21. A computer system for facial detection comprising:
   a memory which stores instructions;
   one or more processors attached to the memory wherein the one or more processors when executing the instructions which are stored, are configured to:
      obtain a video that includes a face;
      perform face detection to initialize locations for a first set of facial landmarks within a first frame from the video containing an image of the face wherein the face detection comprises:
         performing facial landmark detection within the first frame from the video; and
         estimating a rough bounding box for the face based on the facial landmark detection;
      refine the locations for the first set of facial landmarks based on localized information around the first set of facial landmarks;
      estimate future locations for landmarks within the first set of facial landmarks for a future frame from the first frame; and
      train a classifier for a video clip for facial detection, wherein the training includes generating a scaled version of the image of the face directly from an initial frame, wherein the video is a chronological series of frames and the initial frame is an earliest frame containing the face in the chronological series of frames.

22. The method of claim 1 wherein generating a scaled version of the image of the face comprises generating a zoomed-in or enlarged version of the image.

23. The method of claim 1 wherein generating a scaled version of the image of the face comprises generating a zoomed-out or shrunken version of the image.

24. The method of claim 7 wherein the refining the second set of locations for the second set of facial landmarks includes centering location points on the second set of facial landmarks.

25. The method of claim 1 wherein the future frame is a subsequent frame in the chronological series of frames from the first frame.

26. The method of claim 1 wherein the first frame from the video is the initial frame.

* * * * *